(12) United States Patent  (10) Patent No.: US 9,192,430 B2
Rachlin et al.  (45) Date of Patent: Nov. 24, 2015

(54) ELECTROSURGICAL INSTRUMENT WITH TIME LIMIT CIRCUIT

(75) Inventors: Thomas Rachlin, Boulder, CO (US); Aaron Willoughby, Superior, CO (US); Robert Sharp, Boulder, CO (US); Brian Totte, The Woodlands, TX (US); Jeffrey D. Payne, Pueblo, CO (US); Jaime Pinon, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 276 days.

(21) Appl. No.: 12/434,382

(22) Filed: May 1, 2009

(65) Prior Publication Data

US 2010/0280511 A1  Nov. 4, 2010

(51) Int. Cl.
A61B 18/04 (2006.01)
A61B 18/14 (2006.01)
A61B 18/12 (2006.01)
A61B 17/29 (2006.01)
A61B 18/00 (2006.01)

(52) U.S. Cl.
CPC ......... *A61B 18/1445* (2013.01); *A61B 18/1206* (2013.01); *A61B 18/14* (2013.01); *A61B 2017/2945* (2013.01); *A61B 2018/0063* (2013.01); *A61B 2018/00178* (2013.01); *A61B 2018/00345* (2013.01); *A61B 2018/00404* (2013.01); *A61B 2018/00601* (2013.01); *A61B 2018/00619* (2013.01); *A61B 2018/1432* (2013.01)

(58) Field of Classification Search
CPC .................. A61B 2017/00482; A61B 18/1445; A61B 2019/448
USPC .................... 606/27–34, 41–42; 607/101–105
See application file for complete search history.

(56) References Cited

U.S. PATENT DOCUMENTS

| 5,160,334 | A | 11/1992 | Billings et al. |
| 5,312,401 | A | 5/1994 | Newton et al. |
| 5,400,267 | A * | 3/1995 | Denen .................... A61B 17/00 128/908 |
| 5,688,269 | A | 11/1997 | Newton et al. |
| 5,830,212 | A | 11/1998 | Cartmell et al. |
| 6,063,075 | A | 5/2000 | Mihori |
| 6,203,541 | B1 | 3/2001 | Keppel |
| 6,331,181 | B1 * | 12/2001 | Tierney .............. A61B 19/2203 600/429 |
| 6,409,722 | B1 | 6/2002 | Hoey et al. |
| 6,537,272 | B2 * | 3/2003 | Christopherson ...... A61B 18/14 606/34 |
| 6,736,810 | B2 | 5/2004 | Hoey et al. |
| 6,849,073 | B2 | 2/2005 | Hoey et al. |
| 7,169,144 | B2 | 1/2007 | Hoey et al. |
| 2005/0283148 | A1 | 12/2005 | Janssen |
| 2007/0049914 | A1 | 3/2007 | Eggleston |
| 2009/0065565 | A1 | 3/2009 | Cao |

OTHER PUBLICATIONS

International Search Report EP10161596 dated Jul. 28, 2010.

* cited by examiner

Primary Examiner — Phillip Gray

(57) ABSTRACT

An electrosurgical instrument includes a housing having a treatment portion attached thereto. The treatment portion is adapted to connect to an electrosurgical generator that supplies energy to the electrosurgical instrument. An activation element is included and is disposed in electrical communication with the electrosurgical generator and the treatment portion. The activation element is selectively actuatable to supply energy from the electrosurgical generator to the treatment portion. A time-out device is coupled to the housing and is configured to prevent re-use of the electrosurgical instrument after a pre-determined time limit.

23 Claims, 22 Drawing Sheets

ELECTROSURGICAL INSTRUMENT WITH TIME LIMIT CIRCUIT

BACKGROUND

The present disclosure relates to an electrosurgical instrument and more particularly, the present disclosure relates to an endoscopic bipolar electrosurgical forceps for sealing and/or cutting large tissue structures that includes a time limiting circuit to prevent re-use of the device after a pre-set time duration.

TECHNICAL FIELD

Electrosurgical forceps utilize both mechanical clamping action and electrical energy to affect hemostasis by heating the tissue and blood vessels to coagulate, cauterize and/or seal tissue. Many surgical procedures require cutting and/or ligating large blood vessels and large tissue structures. Due to the inherent spatial considerations of the surgical cavity, surgeons often have difficulty suturing vessels or performing other traditional methods of controlling bleeding, e.g., clamping and/or tying-off transected blood vessels or tissue. By utilizing an elongated electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, larger vessels can be more difficult to close using these standard techniques.

During the course of surgical procedure, a surgeon may employ a variety of different instrumentation, including both reusable instruments and disposables instrument. The manufacturer's intent with a disposable instrument is for the surgeon or surgical personnel to discard the disposable instrument after a given surgical procedure since the disposable instrument in most cases may not be sterilized using conventional sterilizing techniques. However, in some instances there may be a temptation to re-use disposable instruments to save costs especially in clinic-type environments or low-income areas. Obviously, issues and health concerns arise when disposable instruments are re-used for surgical purposes.

SUMMARY

The present disclosure relates to an electrosurgical instrument that includes a housing having a treatment portion attached thereto that is adapted to connect to an electrosurgical generator that supplies energy thereto. An activation element is disposed in electrical communication with the electrosurgical generator and the treatment portion and is selectively actuatable to supply energy from the electrosurgical generator to the treatment portion. A time-out device is coupled to the housing and is configured to prevent re-use of the electrosurgical instrument after a pre-determined time limit.

In one embodiment, the time out device includes a timing circuit in electrical communication with the electrosurgical generator. The timing circuit is initiateable upon initial activation of the electrosurgical instrument and is configured to prevent re-use of the electrosurgical instrument after a pre-determined time limit. The timing circuit may be initiateable upon removal of a timing pin, an electrically insulative cover and/or a battery sleeve. In one embodiment, the timing circuit actively prevents activation of the electrosurgical generator or activation element after a predetermined time limit, e.g., shorts out the electrosurgical instrument or the activation element.

In another embodiment, the time out device includes a mechanical lockout, an optical lockout and/or an electrical lockout. For example, the time out device may include a mechanical lockout that decays when exposed to ambient air, temperature and/or fluid.

In yet another embodiment, the time out device includes an indicator that appears after a pre-determined time limit to indicate that the electrosurgical instrument is compromised, e.g., non-sterile, already used, contaminated, etc. The indicator may include a color-code, indicia and/or bar code that is readable by the electrosurgical generator or the surgeon to prevent re-use of the instrument.

The present disclosure also relates to an electrosurgical instrument that includes a housing having a treatment portion attached thereto and an activation element that is disposed in electrical communication with the electrosurgical generator and the treatment portion. The activation element is selectively actuatable to supply energy from the electrosurgical generator to the treatment portion. A smart connector is connected to the housing and is adapted to connect to the electrosurgical generator. A time-out device is coupled to the smart connector and is configured to prevent re-use of the electrosurgical instrument after a pre-determined time limit. The time out device may include a mechanical lockout that decays when exposed to ambient air, temperature and/or fluid, an optical lockout that prevents activation of the electrosurgical generator when activated and/or an electrical lockout that shorts the instrument to prevent re-use.

In one embodiment, the time out device includes an indicator e.g., a color-code, indicia or a bar code that appears after a pre-determined time limit to indicate that the electrosurgical instrument is compromised. The indicator may be readable by the generator to prevent activation thereof.

The present disclosure also relates to an electrosurgical instrument, includes a housing having a treatment portion attached thereto, the treatment portion adapted to connect to an electrosurgical generator that supplies energy thereto and a device activation and use limiting circuit. The device activation and use limiting circuit includes an activation circuit, a timer circuit and a control relay connected therebetween. The activation circuit is configured to relay at least one parameter to the electrosurgical generator. The timer circuit configured to prevent re-use of the electrosurgical instrument after a pre-determined time limit. The control relay is also configured to disable the activation circuit after the pre-determined time limit is exceeded. The activation circuit may further include an activation switch configured to indicate activation of the treatment portion.

The timer circuit may include a timer power supply, a timing device configured to determine it the pre-determined time limit has been exceeded, and a timer enable switch configured to connect the timer power supply to the timing device. The electrosurgical instrument is made inoperable if the pre-determined time limit has been exceeded.

In another embodiment the timer enable switch, when activated, cannot be deactivated. The timer enable switch may include a removal pull tab configured enable the timer enable switch when removed therefrom. The timing device may include an off-timer or a microcontroller.

BRIEF DESCRIPTION OF THE DRAWINGS

Various embodiments of the subject instrument are described herein with reference to the drawings wherein.

DETAILED DESCRIPTION

Figure 1A:
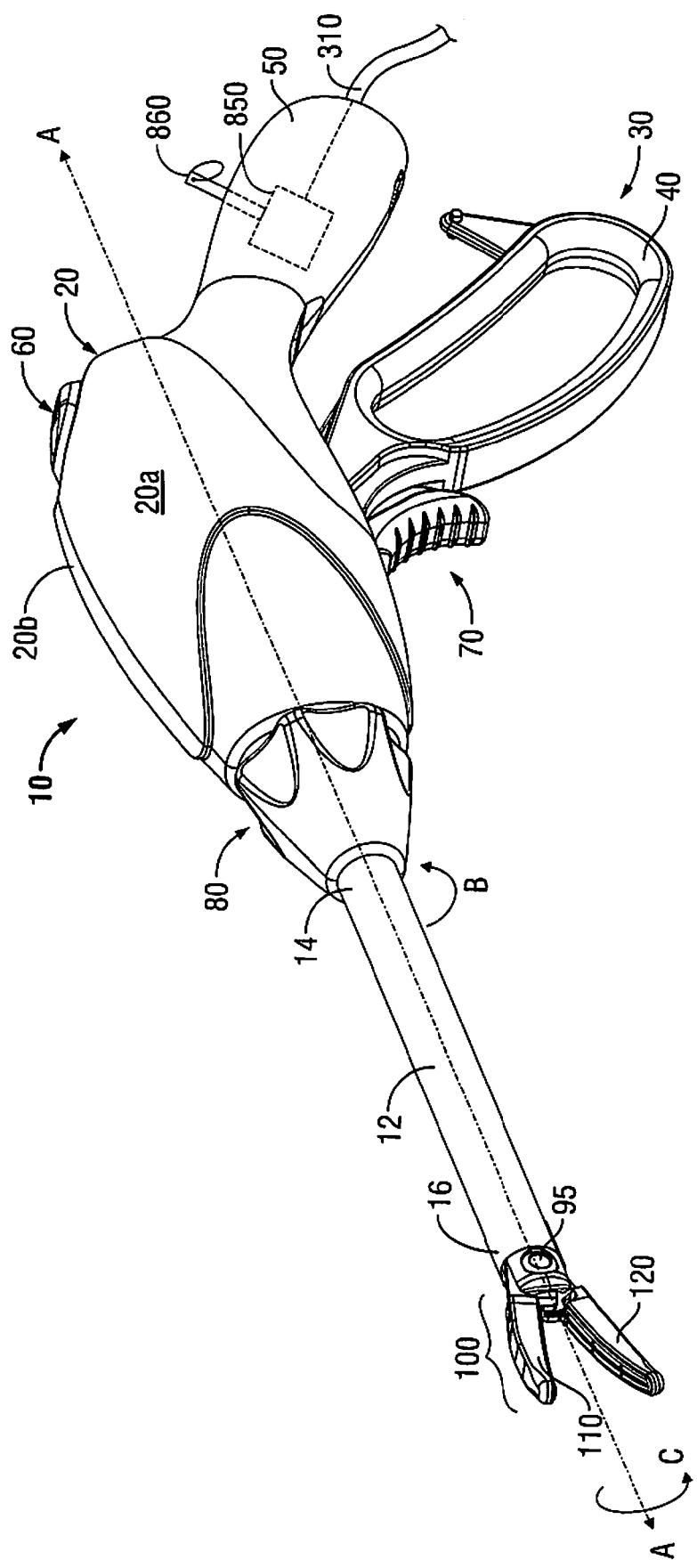
FIG. 1A is a perspective view of a bipolar forceps shown in open configuration and including a housing, a shaft, handle assembly, trigger assembly and an end effector assembly according to the present disclosure.
Figure 1B:
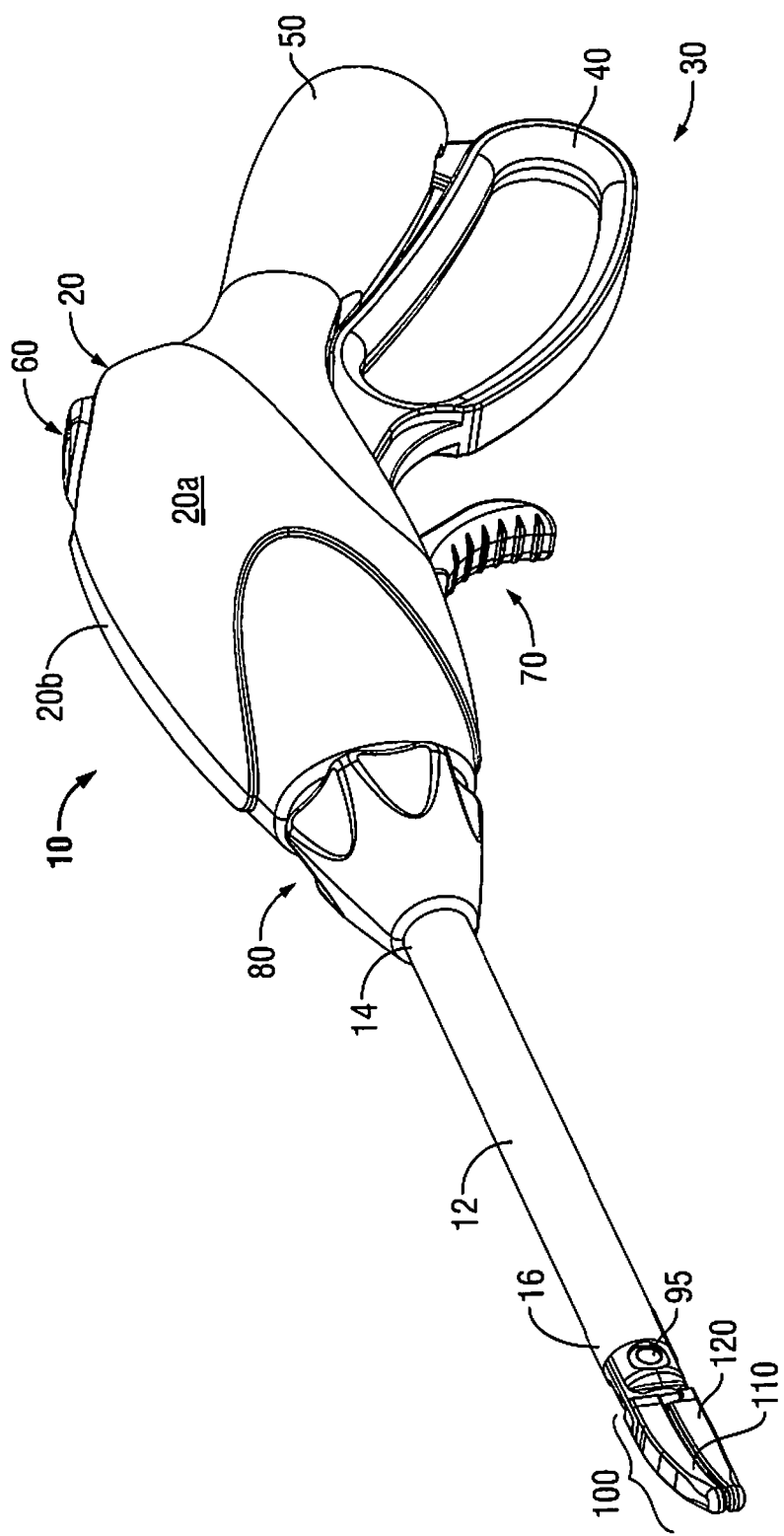
FIG. 1B is a perspective view of the bipolar forceps of FIG. 1A shown in closed configuration.
Figure 2:
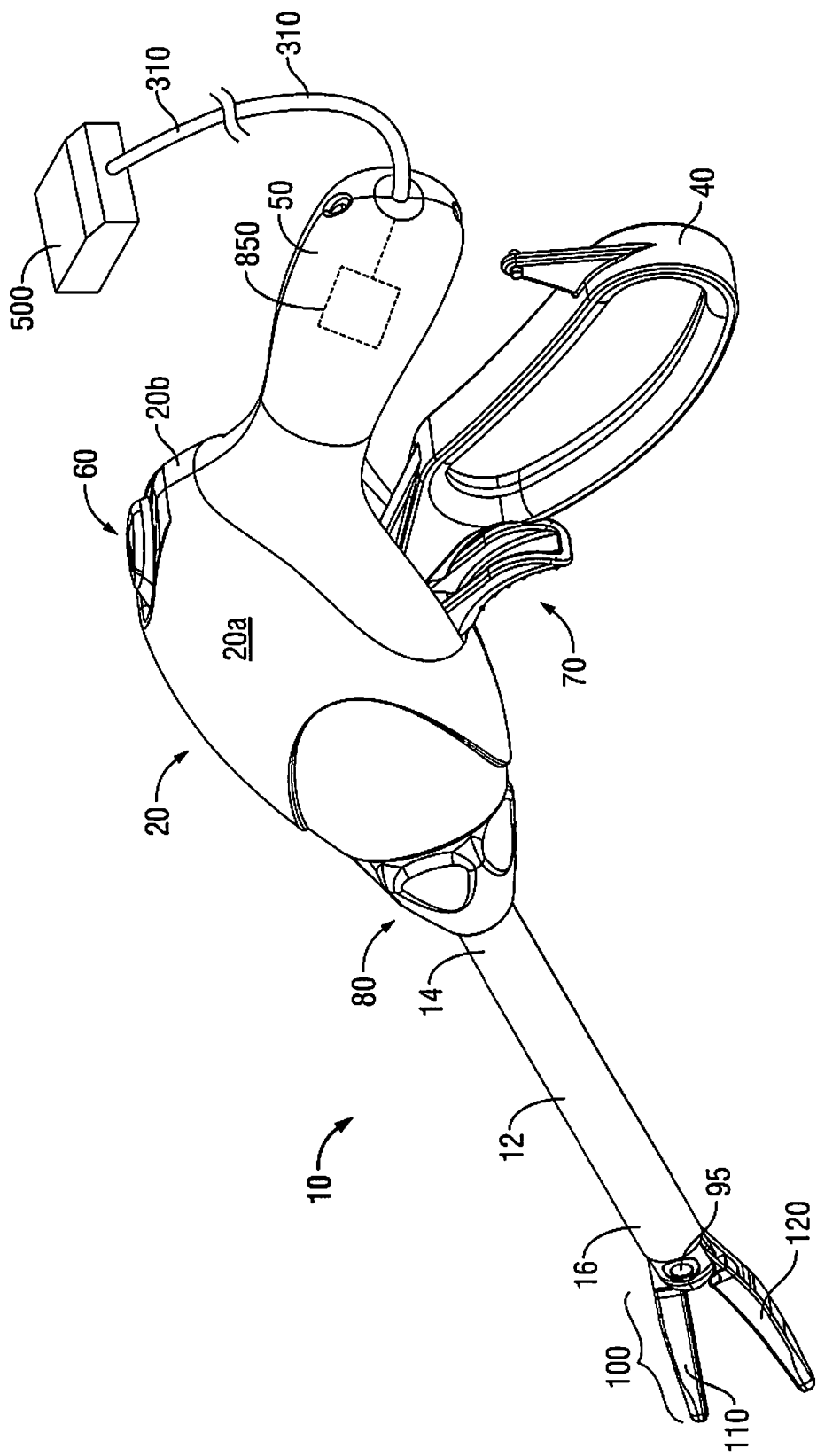
FIG. 2 is a rear view of the forceps of FIG. 1A.

Turning now to FIGS. 1A-2, one embodiment of a bipolar forceps 10 is shown for use with various surgical procedures and generally includes a housing 20, a handle assembly 30, a rotating assembly 80, a trigger assembly 70 and an end effector assembly 100 which mutually cooperate to grasp, seal and divide large tubular vessels and large vascular tissues. Although the majority of the figure drawings depict a bipolar forceps 10 for use in connection with endoscopic surgical procedures, the present disclosure and method described herein may be used for more traditional open surgical procedures. Moreover, other types of surgical instruments may be configured to incorporate one or more aspects of the present disclosure. For the purposes herein, the forceps 10 is described in terms of an endoscopic instrument; however, it is contemplated that an open version of the forceps may also include the same or similar operating components and features as described below.

Forceps 10 includes a shaft 12 which has a distal end 16 dimensioned to mechanically engage the end effector assembly 100 and a proximal end 14 which mechanically engages the housing 20. Details of how the shaft 12 connects to the end effector are described in more detail with respect to U.S. patent application Ser. No. 11/595,194 entitled "VESSEL SEALER AND DIVIDER FOR LARGE TISSUE STRUCTURES", the entire contents of which are incorporated by reference herein. In the drawings and in the descriptions which follow, the term "proximal," as is traditional, will refer to the end of the forceps 10 which is closer to the user, while the term "distal" will refer to the end which is farther from the user.

As best seen in FIG. 2, forceps 10 also includes an electrosurgical cable 310 which connects the forceps 10 to a source of electrosurgical energy, e.g., a generator 500 (shown schematically). It is contemplated that generators such as those sold by Valleylab—a division of Covidien LP, located in Boulder Colo. may be used as a source of electrosurgical energy, e.g., Ligasure™ Generator, FORCE TRIAD® Electrosurgical Generator, FORCE EZ™ Electrosurgical Generator, FORCE FX™ Electrosurgical Generator, FORCE 1C™, FORCE 2™ Generator, SurgiStat™ II or other envisioned generators which may perform different or enhanced functions. The generator 500 includes various safety and performance features including isolated output, independent activation of accessories.

Figure 7A:
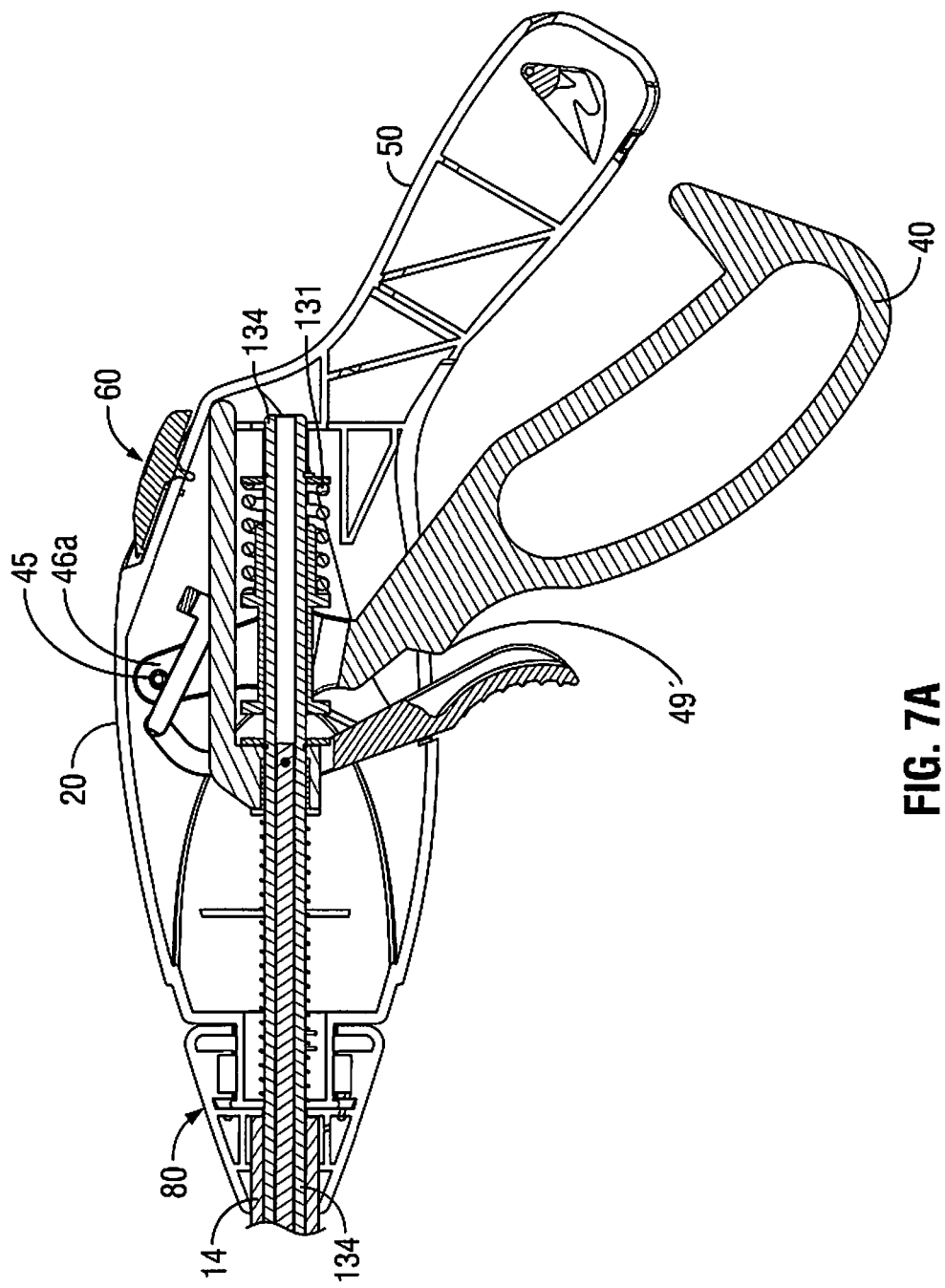
FIG. 7A is side cross-sectional view of the housing showing both the trigger and the handle un-actuated.
Figure 7B:
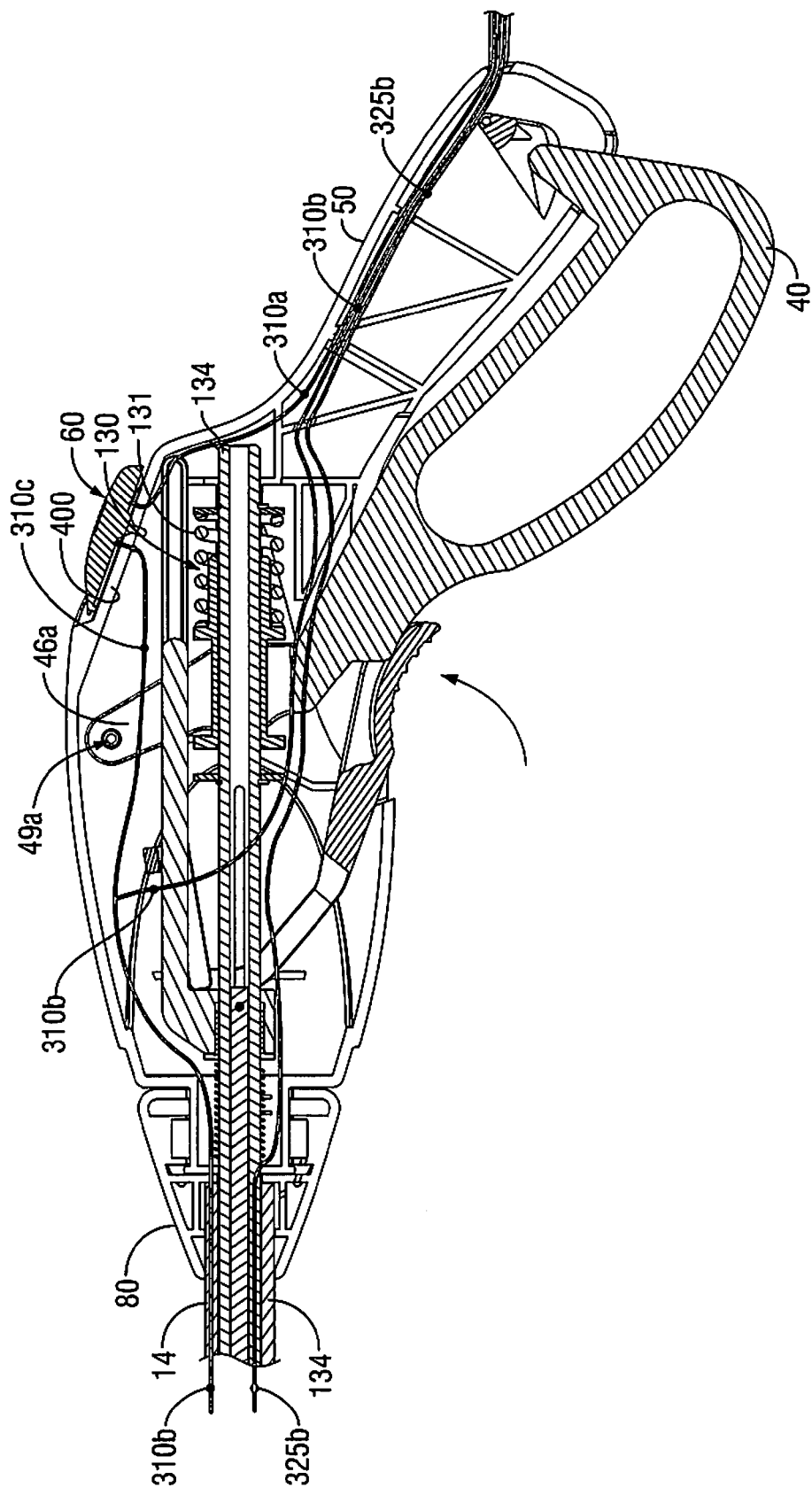
FIG. 7B is side cross-sectional view of the housing showing both the trigger and the handle actuated.

Cable 310 is internally divided into cable leads 310a, 310b and 325b which are designed to transmit electrical potentials through their respective feed paths through the forceps 10 to the end effector assembly 100 (See FIG. 7B). Details relating to the electrical connections are explained in more detail below with respect to the above-identified patent application or, alternatively, with respect to U.S. patent application Ser. No. 11/540,335 entitled "IN-LINE VESSEL SEALER AND DIVIDER" the entire contents of which are incorporated by reference herein.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is operatively associated with the housing 20 and is rotatable about a longitudinal axis "A-A" (See FIG. 1A) defined through forceps 10. Details of the rotating assembly 80 are described in more detail with respect to above-identified U.S. patent application Ser. No. 11/595,194.

As mentioned above, end effector assembly 100 is attached at the distal end 16 of shaft 12 and includes a pair of opposing jaw members 110 and 120. Movable handle 40 of handle assembly 30 is ultimately connected to a drive assembly 130 (See FIG. 4A) which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed.

Figure 4A:
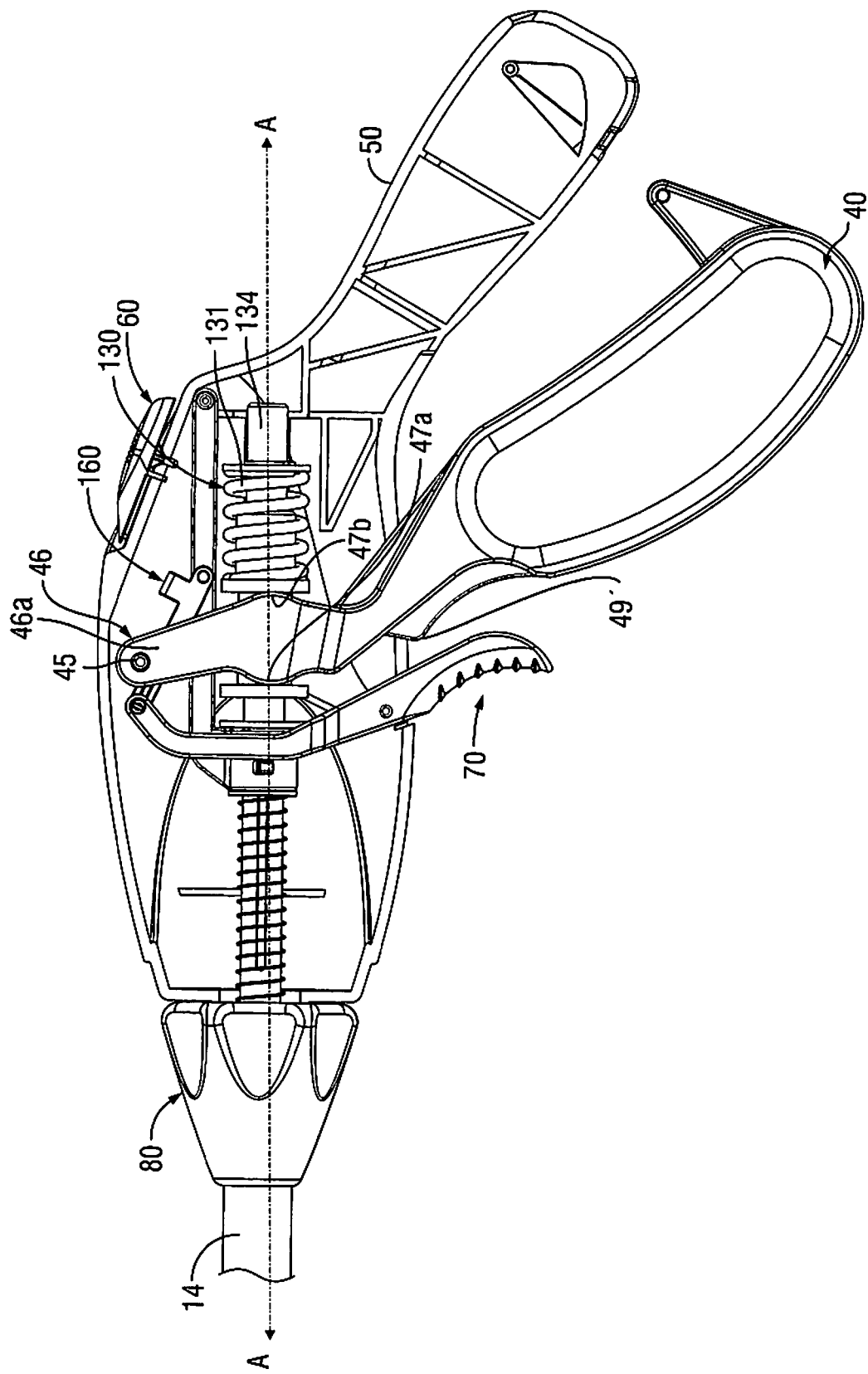
FIG. 4A is side view of the endoscopic forceps of FIG. 1A with the internal working components of the forceps exposed.
Figure 4B:
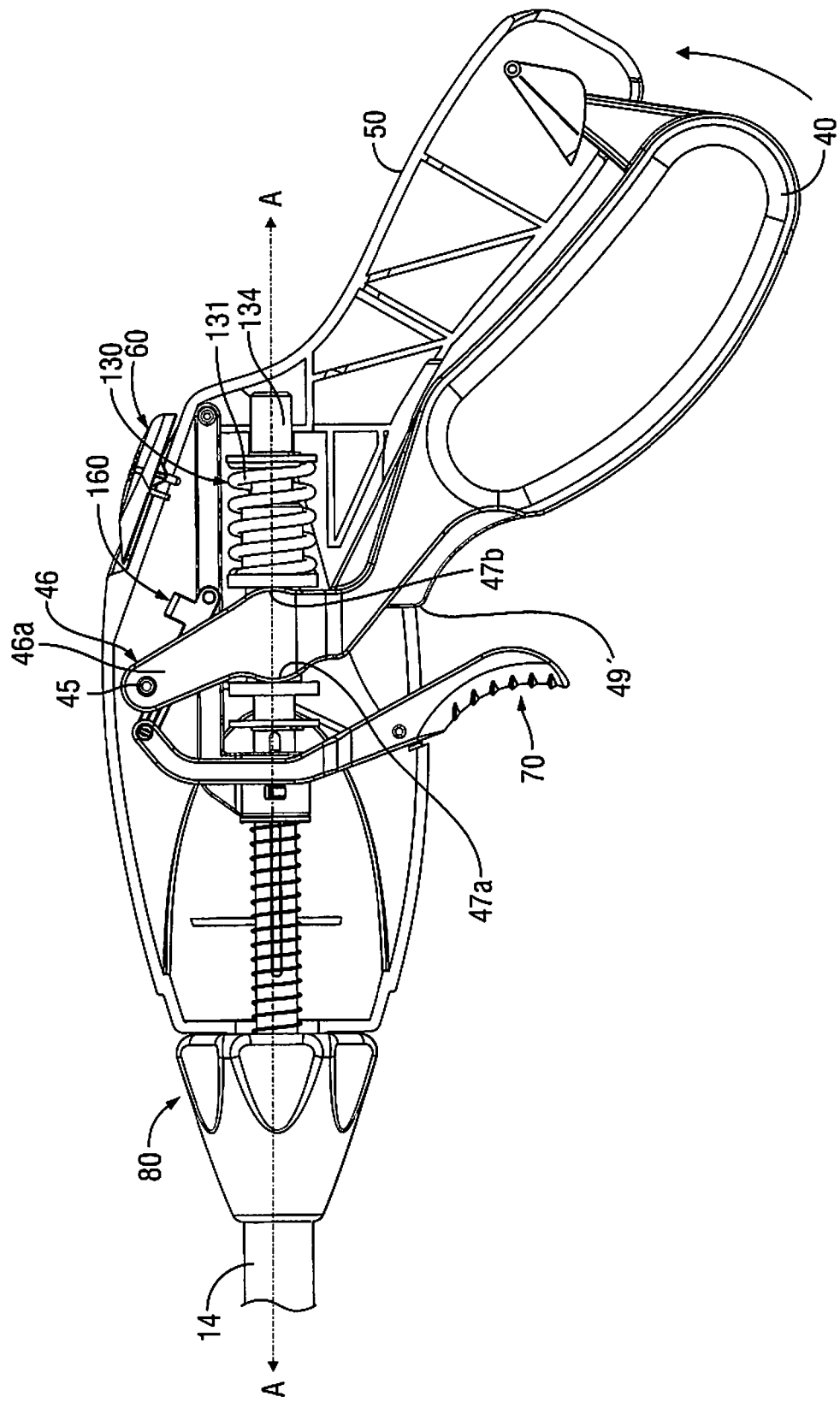
FIG. 4B is side view of the endoscopic forceps of FIG. 1B with the internal working components of the forceps exposed.

With respect to the actuation of the instrument and as best seen in FIGS. 4A and 4B, movable handle 40 is selectively movable about a pivot pin 45 from a first position relative to fixed handle 50 to a second position in closer proximity to the fixed handle 50 which, as explained below, imparts movement of the jaw members 110 and 120 relative to one another. The movable handle includes a clevis 46 which forms a pair of upper flanges 46a and 46b each having an aperture at an upper end thereof for receiving a pivot pin 45 (See FIG. 10) therethrough and mounting the upper end of the handle 40 to the housing 20. In turn, pivot pin 45 mounts to respective housing halves 20a and 20b. Pivot pin 45 is dimensioned to mount within socket 45b of housing half 20a (See FIG. 10).

Figure 6:
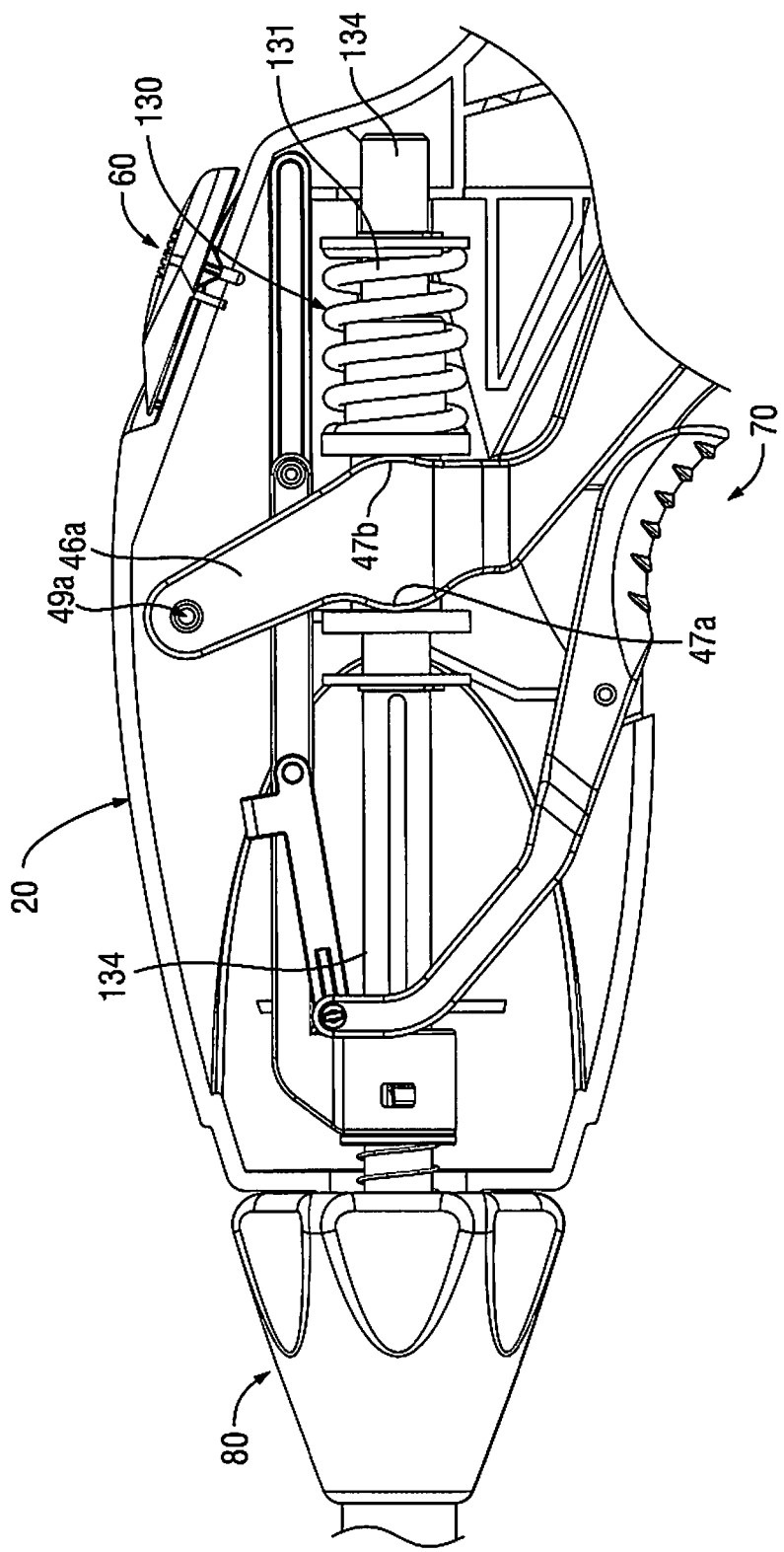
FIG. 6 is an internal, side view of the endoscopic forceps of FIG. 1B with the trigger shown in an actuated position.

Each upper flange 46a and 46b also includes a force-actuating flange or drive flange 47a and 47b (See FIG. 6), respectively, which are aligned along longitudinal axis "A" and which abut the drive assembly 130 such that pivotal movement of the handle 40 forces actuating flanges 47a and 47b against the drive assembly 130 which, in turn, closes the jaw members 110 and 120 (See FIGS. 4A and 4B). A more detailed explanation of the inter-cooperating components of the handle assembly 30 and the drive assembly 130 is discussed with respect to U.S. patent application Ser. No. 11/595,194.

As shown best in FIGS. 3A-3F, 11 and 12, the end effector assembly 100 includes opposing jaw members 110 and 120 which cooperate to effectively grasp tissue for sealing purposes. The end effector assembly 100 is designed as a bilateral assembly, i.e., both jaw members 110 and 120 pivot relative to one another about a pivot pin 95 disposed therethrough. The jaw members 110 and 120 are curved to facilitate manipulation of tissue and to provide better "line of sight" for accessing organs and large tissue structures.

A reciprocating drive sleeve 134 is slidingly disposed within the shaft 12 and is remotely operable by the drive assembly 130 as explained in more with respect to U.S. patent application Ser. No. 11/595,194. As can be appreciated, squeezing handle 40 toward handle 50 pulls drive sleeve 134 and drive pin 139 proximally to close the jaw members 110 and 120 about tissue grasped therebetween and pushing the sleeve 134 distally opens the jaw members 110 and 120 for grasping purposes.

Turning back to the details of the jaw member 110 and 120 as best shown in FIGS. 3A-3F, jaw member 110 includes a support base 119 which extends distally from flange 113 and which is dimensioned to support an insulative plate 119' thereon. Insulative plate 119', in turn, is configured to support an electrically conductive tissue engaging surface or sealing plate 112 thereon. Outer housing 116 includes a cavity 116a which is dimensioned to securely engage the electrically conductive sealing surface 112 as well as the support base 119 and insulative plate 119'. It is envisioned that lead 310b which extends from switch 60 (See FIG. 7B) terminates within the outer insulator 116 and is designed to electro-mechanically couple to the sealing plate 112 by virtue of a crimp-like connection 326a. Insulator 119', electrically conductive sealing surface 112 and the outer, non-conductive jaw housing 116 are dimensioned to limit and/or reduce many of the known undesirable effects related to tissue sealing, e.g., flashover, thermal spread and stray current dissipation.

Figure 3A:
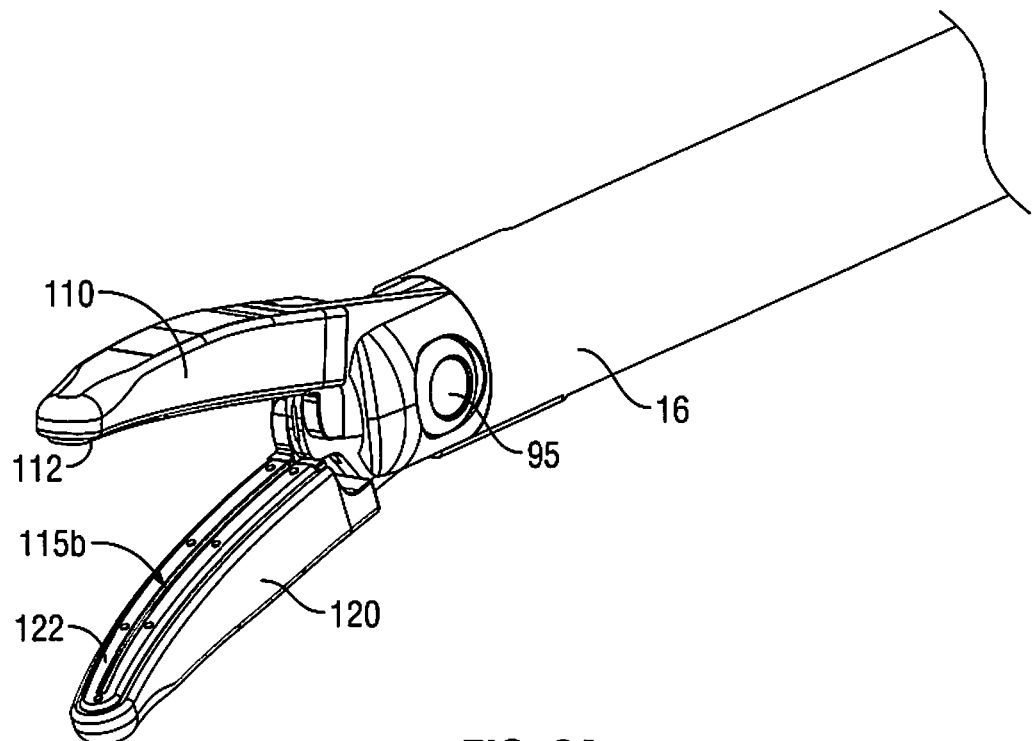
FIG. 3A is an enlarged, front perspective view of the end effector assembly of FIG. 1A shown in an open configuration.
Figure 3B:
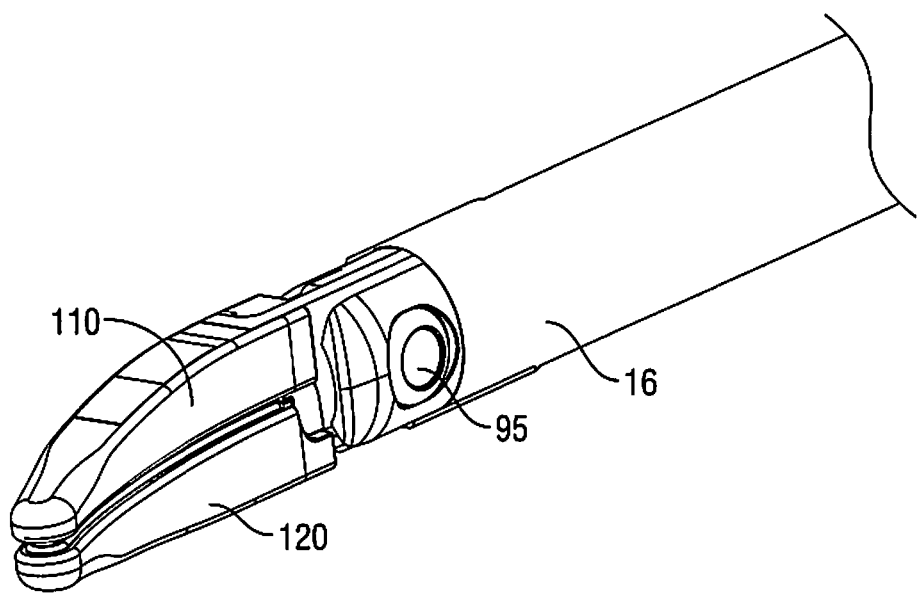
FIG. 3B is an enlarged, front perspective view of the end effector assembly of FIG. 1A shown in a closed configuration.
Figure 3C:
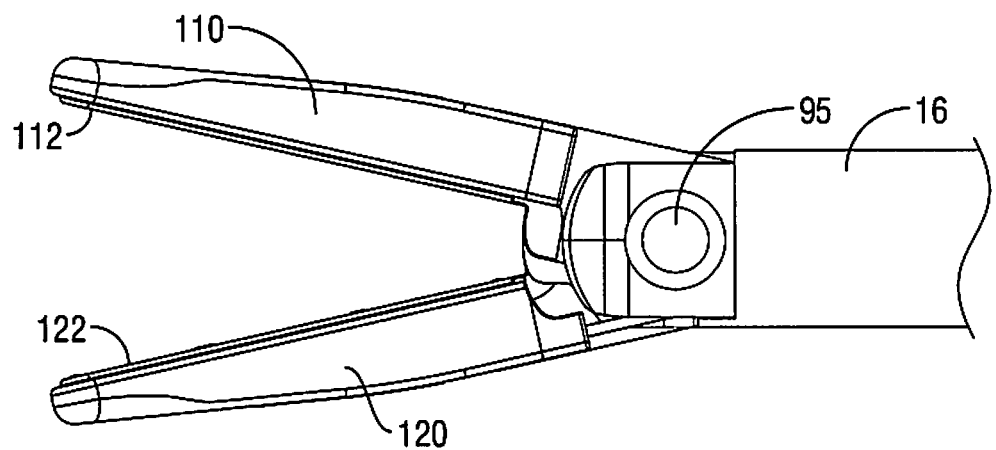
FIG. 3C is an enlarged, side view of the end effector assembly of FIG. 1A shown in open configuration.
Figure 3D:
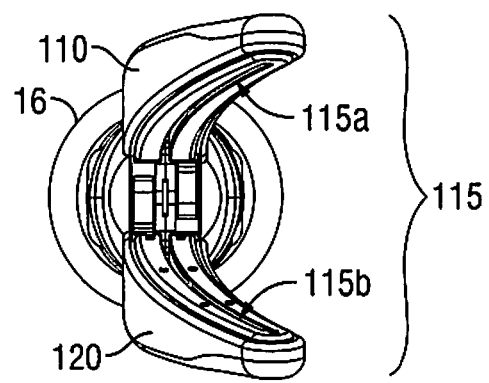
FIG. 3D is an enlarge, front view of the end effector assembly of FIG. 1A shown in open configuration.
Figure 3E:
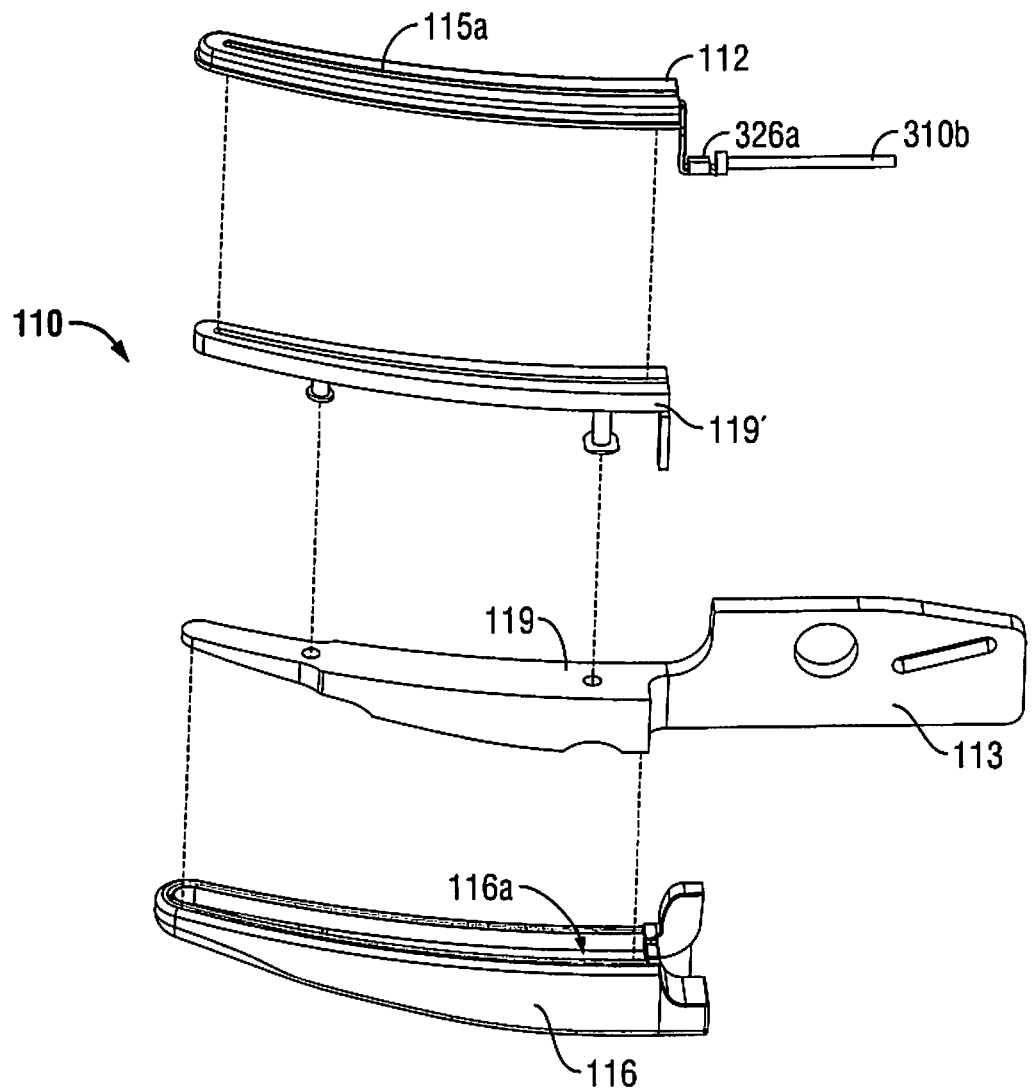
FIG. 3E is a greatly-enlarged, exploded perspective view of the top jaw member.
Figure 11:
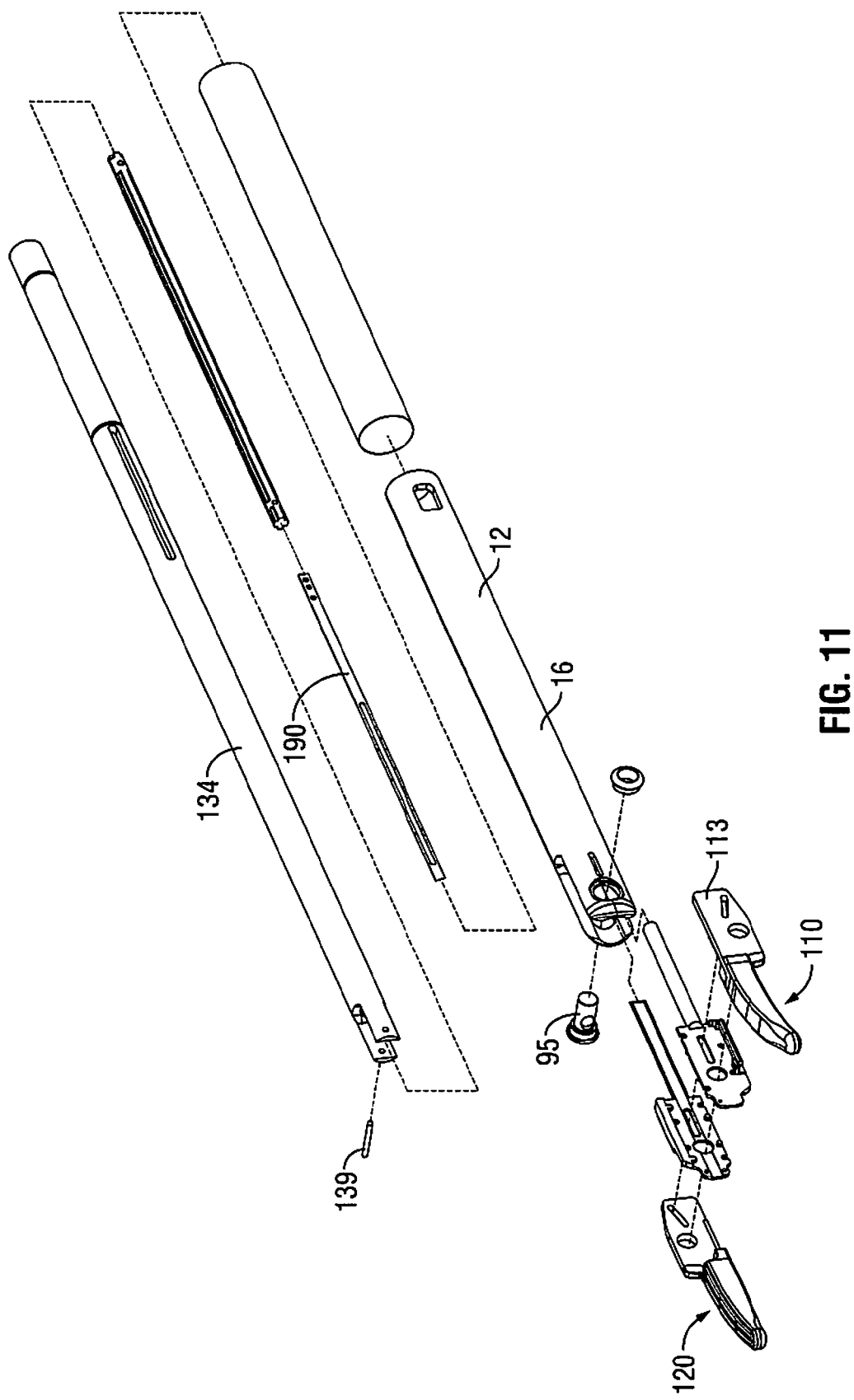
FIG. 11 is an enlarged, exploded perspective view of the end effector assembly and the shaft.
Figure 12:
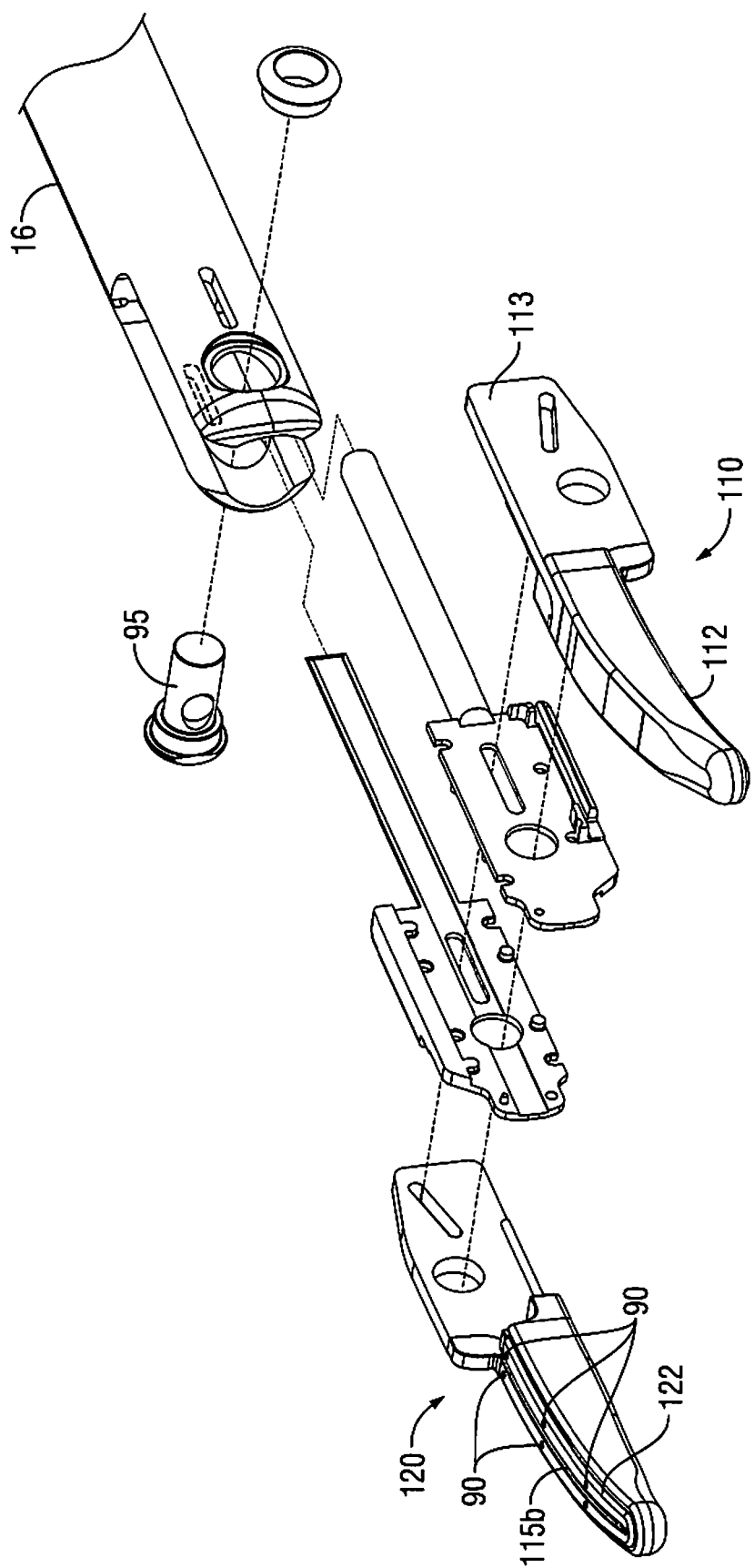
FIG. 12 is a greatly enlarged, exploded perspective view of the end effector assembly.
Figure 13A:
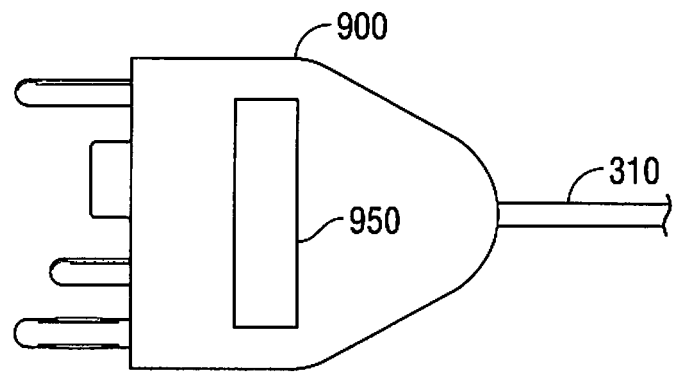
FIGS. 13A-13C show schematic views of various embodiments of a smart connector according to the present disclosure.
Figure 13B:
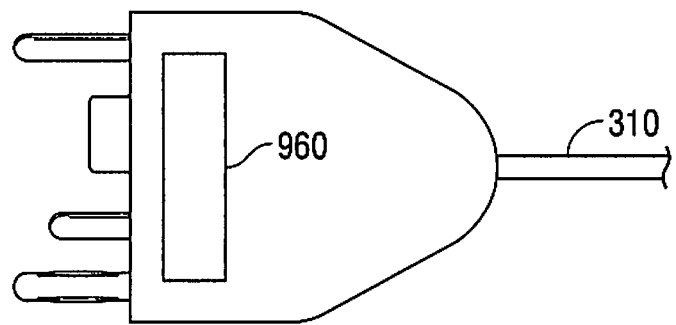
Figure 13C:
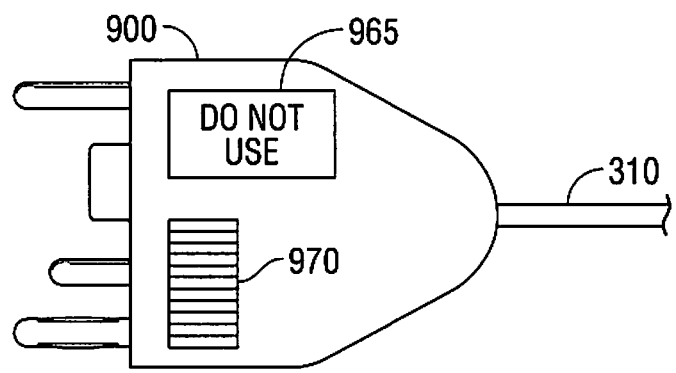

The electrically conductive surface or sealing plate 112 and the outer housing 116, when assembled, form a longitudinally-oriented slot 115a defined therethrough for reciprocation of a knife blade 190 (See FIG. 11). It is envisioned that knife slot 115a cooperates with a corresponding knife slot 115b defined in jaw member 120 to facilitate longitudinal extension of the knife blade 190 along a preferred cutting plane to effectively and accurately separate the tissue along the formed tissue seal. Together, knife slots 115a and 115b form knife channel 115 (See FIG. 4B) for reciprocation of the knife 190. As best illustrated in FIG. 3D, knife channel 115 runs through the center of the jaw members 110 and 120, respectively, such that a blade 190 from the knife assembly 70 can cut the tissue grasped between the jaw members 110 and 120 when the jaw members 110 and 120 are in a closed position. As described in more detail with respect to U.S. patent application Ser. No. 11/595,194 forceps 10 includes a passive lockout flange 49' (See FIG. 4B) which prevents actuation of the knife blade 190 when the handle 40 is open thus preventing accidental or premature activation of the blade 190 through the tissue. In addition, the passive lockout flange 49' is dimensioned to force the trigger 70 to retract the knife 190 when the handle 40 is moved to an open position.

Jaw member 120 includes similar elements to jaw member 110 such as jaw housing 126 which encapsulates a support plate 129, an insulator plate 129' and an electrically conductive sealing surface 122. Likewise, the electrically conductive surface 122 and the insulator plate 129', when assembled, include respective longitudinally-oriented knife slot 115b defined therethrough for reciprocation of the knife blade 190. As mentioned above, when the jaw members 110 and 120 are closed about tissue, knife slots 115a and 115b form a complete knife channel 115 (See FIG. 3D) to allow longitudinal extension of the knife 190 in a distal fashion to sever tissue along a tissue seal. It is also envisioned that the knife channel 115 may be completely disposed in one of the two jaw members, e.g., jaw member 120, depending upon a particular purpose. It is also envisioned that jaw member 120 may be assembled in a similar manner as described above with respect to jaw member 110. More particularly, the sealing plate 122 may be dimensioned to include an outer peripheral rim 122a which is dimensioned to mechanically interface with an inner lip 126b of housing 126 to secure the sealing plate 122 to the housing 126 with plates 129 and 129' encapsulated therein.

Figure 3F:
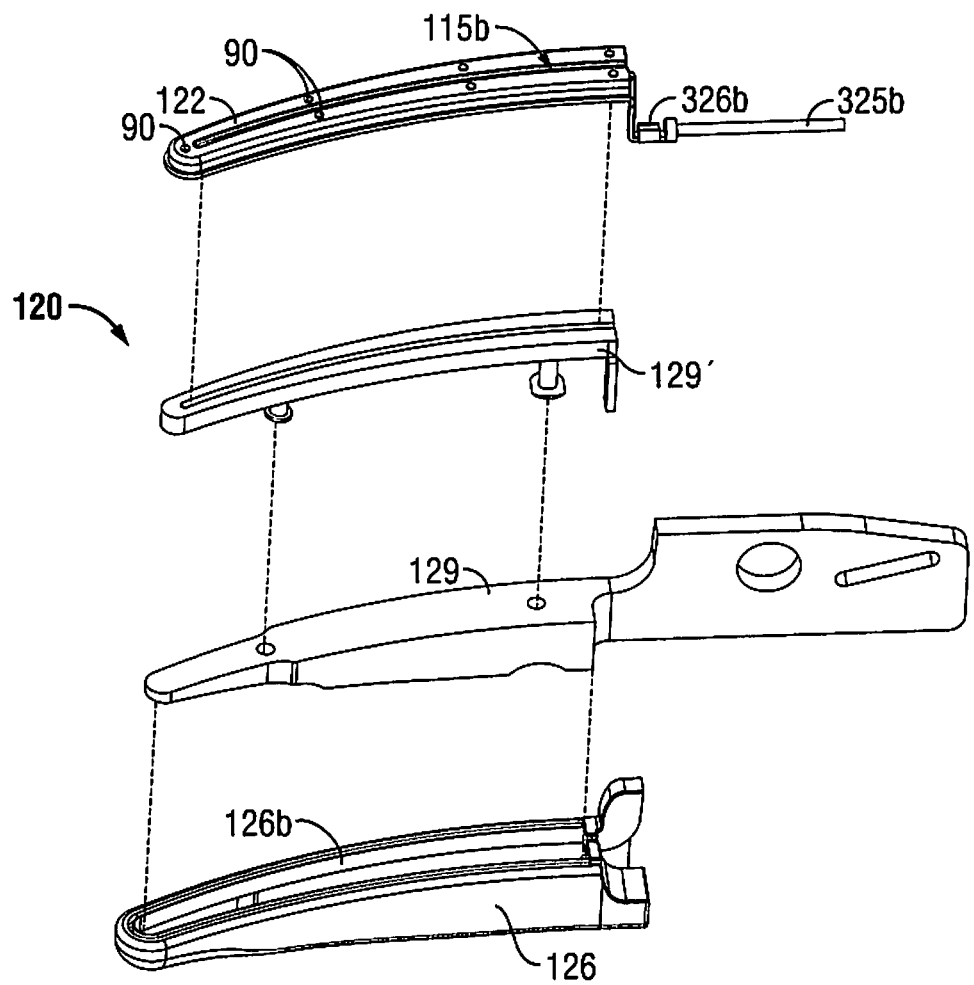
FIG. 3F is a greatly-enlarged, exploded perspective view of the bottom jaw member.
Figure 8:
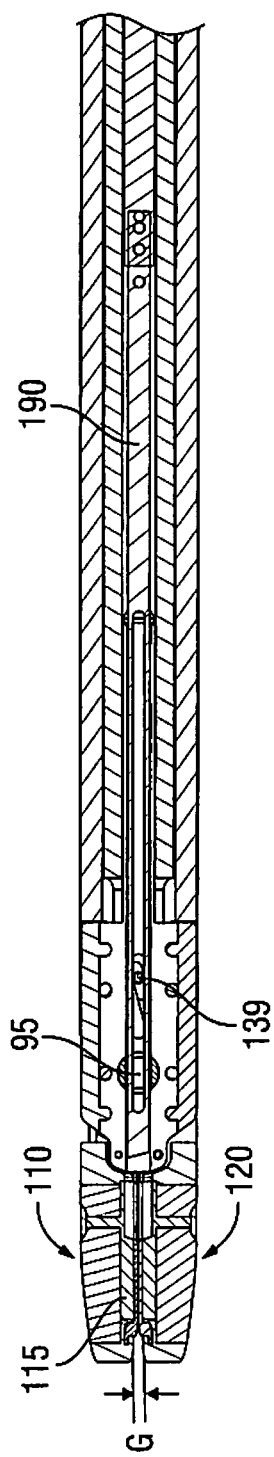
FIG. 8 is an enlarged, side cross-sectional view showing the end effector in a closed position and the knife in an actuated position.

As best seen in FIG. 3F, jaw member 120 includes a series of stop members 90 disposed on the inner facing surface of the electrically conductive sealing surface 122 to facilitate gripping and manipulation of tissue and to define a gap "G" (FIG. 8) between opposing jaw members 110 and 120 during sealing and cutting of tissue. It is envisioned that the series of stop members 90 may be employed on one or both jaw members 110 and 120 depending upon a particular purpose or to achieve a desired result. A detailed discussion of these and other envisioned stop members 90 as well as various manufacturing and assembling processes for attaching and/or affixing the stop members 90 to the electrically conductive sealing surfaces 112, 122 are described in commonly-assigned, co-pending U.S. Pat. No. 7,473,253 entitled "VESSEL SEALER AND DIVIDER WITH NON-CONDUCTIVE STOP MEMBERS" which is hereby incorporated by reference in its entirety herein.

Figure 5A:
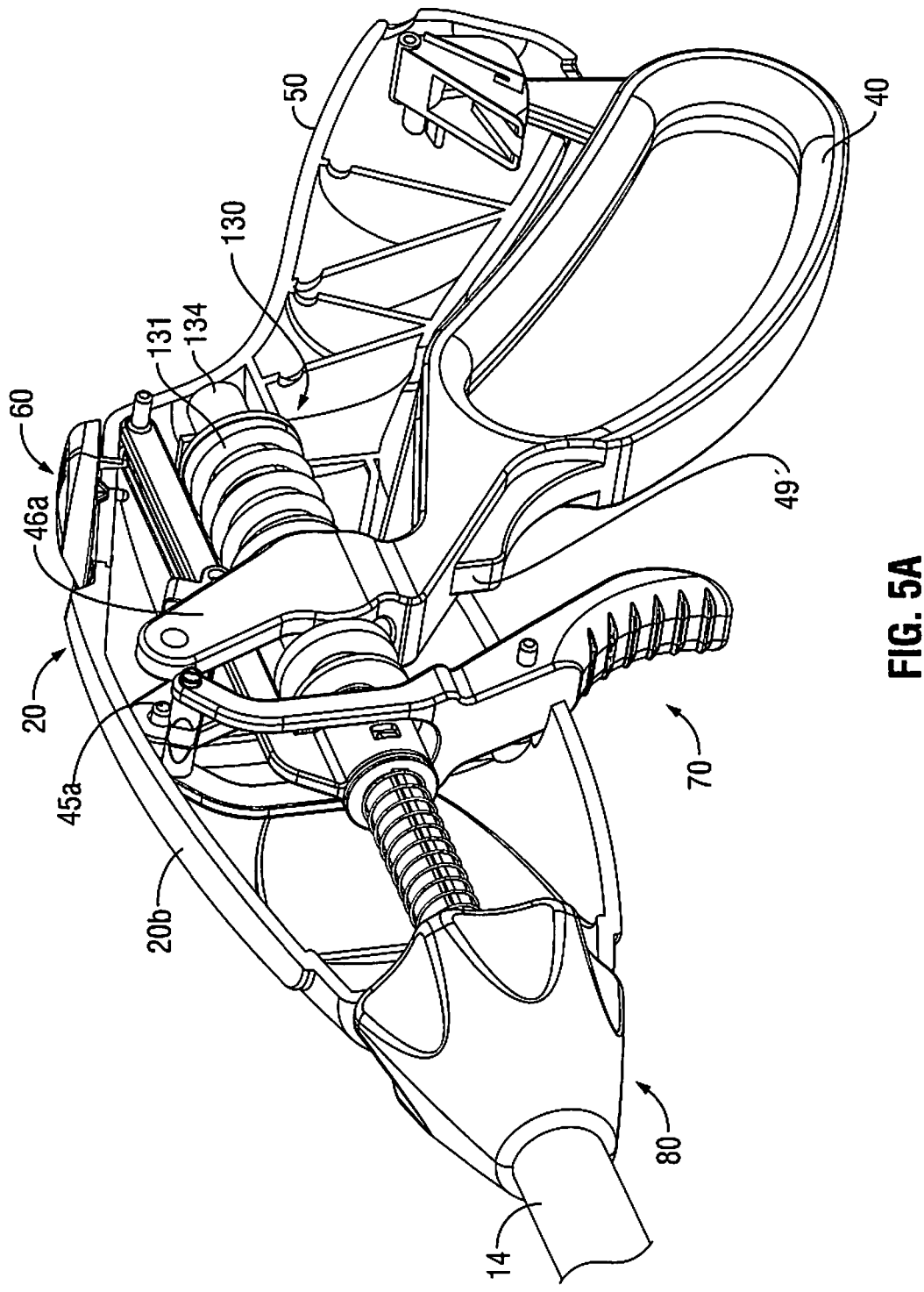
FIG. 5A is an internal, perspective view of the endoscopic forceps of FIG. 1B with the internal working components of the forceps exposed and the trigger shown in an un-actuated position.
Figure 5B:
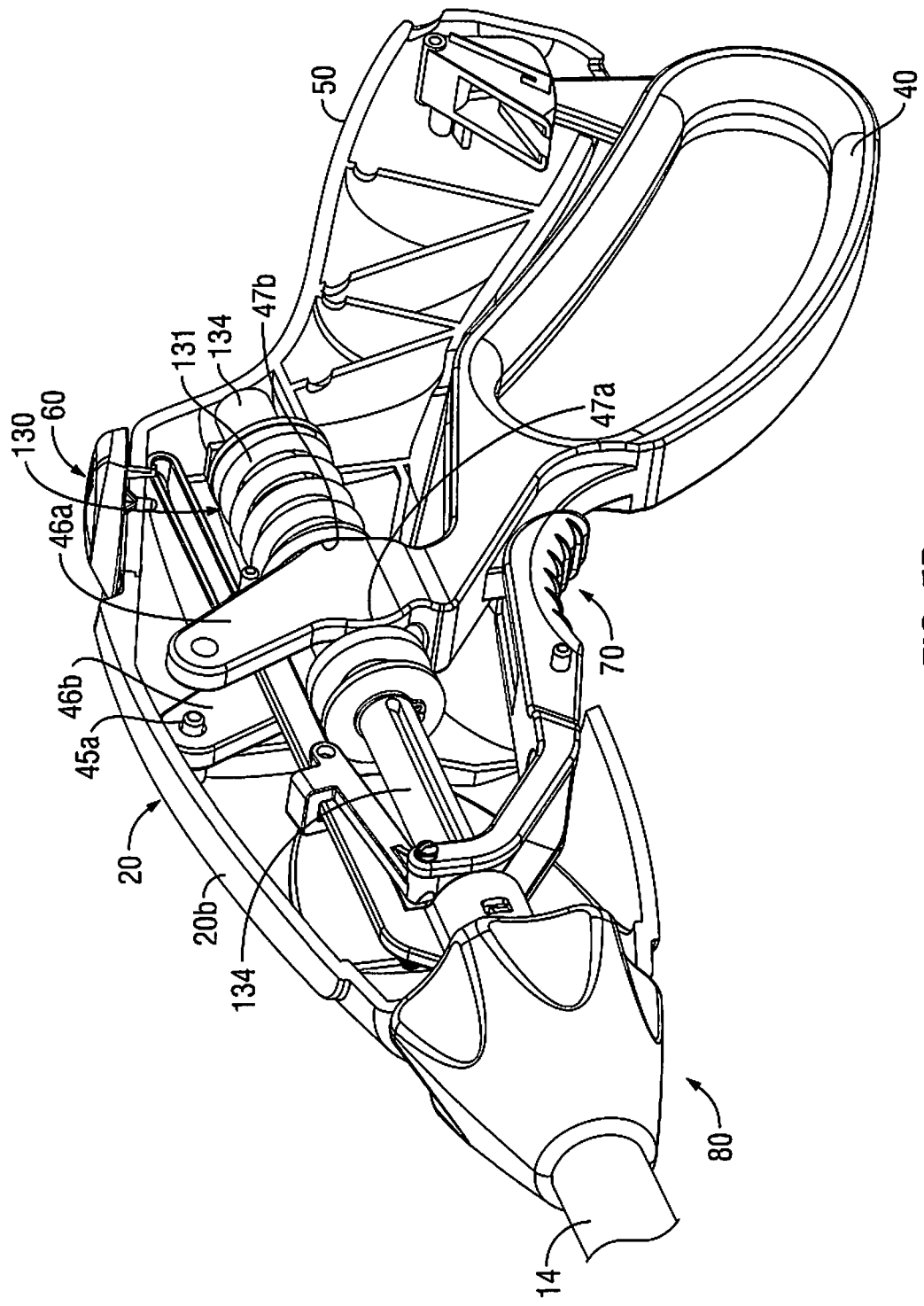
FIG. 5B is an internal, perspective view of the endoscopic forceps of FIG. 1B with the internal working components of the forceps exposed and the trigger shown in an actuated position.

Jaw member 120 is connected to a second electrical lead 325b extending from switch 60 (See FIG. 5B) which terminates within the jaw housing 126 and is designed to electromechanically couple to the sealing plate 122 by virtue of a crimp-like connection 326b. As explained in more detail below, leads 310b and 325b allow a user to selectively supply bipolar electrosurgical energy to the jaw members 110 and 120 as needed during surgery.

Jaw members 110 and 120 are electrically isolated from one another such that electrosurgical energy can be effectively transferred through the tissue to form a tissue seal. Cable leads 310b and 325b are held loosely but securely along the cable path to permit rotation of the jaw members 110 and 120. As can be appreciated, this isolates electrically conductive sealing surfaces 112 and 122 from the remaining operative components of the end effector assembly 100 and shaft 12. The two electrical potentials are isolated from one another by virtue of the insulative sheathing surrounding the cable leads 310b and 325b.

Figure 9:
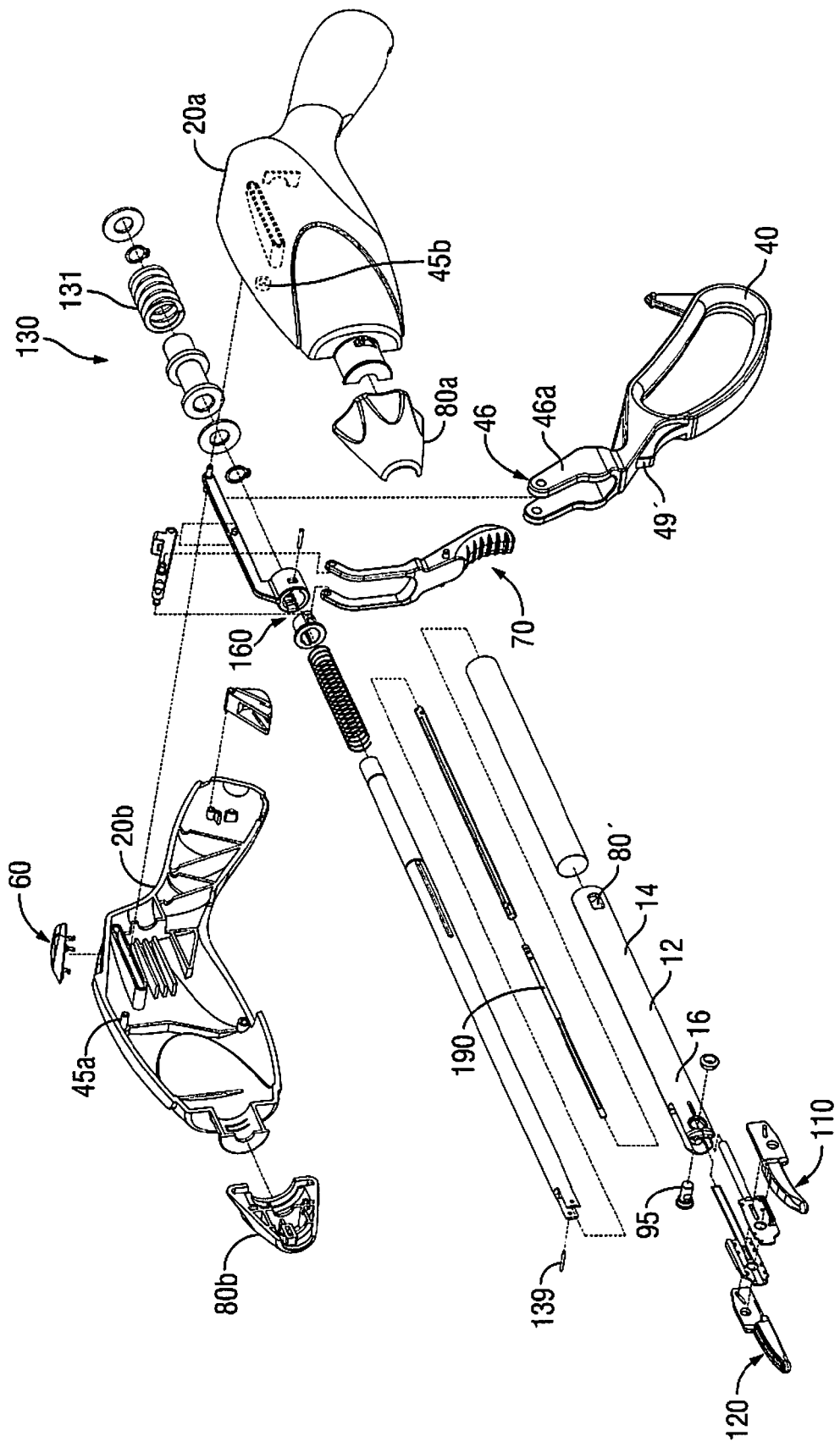
FIG. 9 is an exploded, perspective view of the forceps of FIG. 1A.
Figure 10:
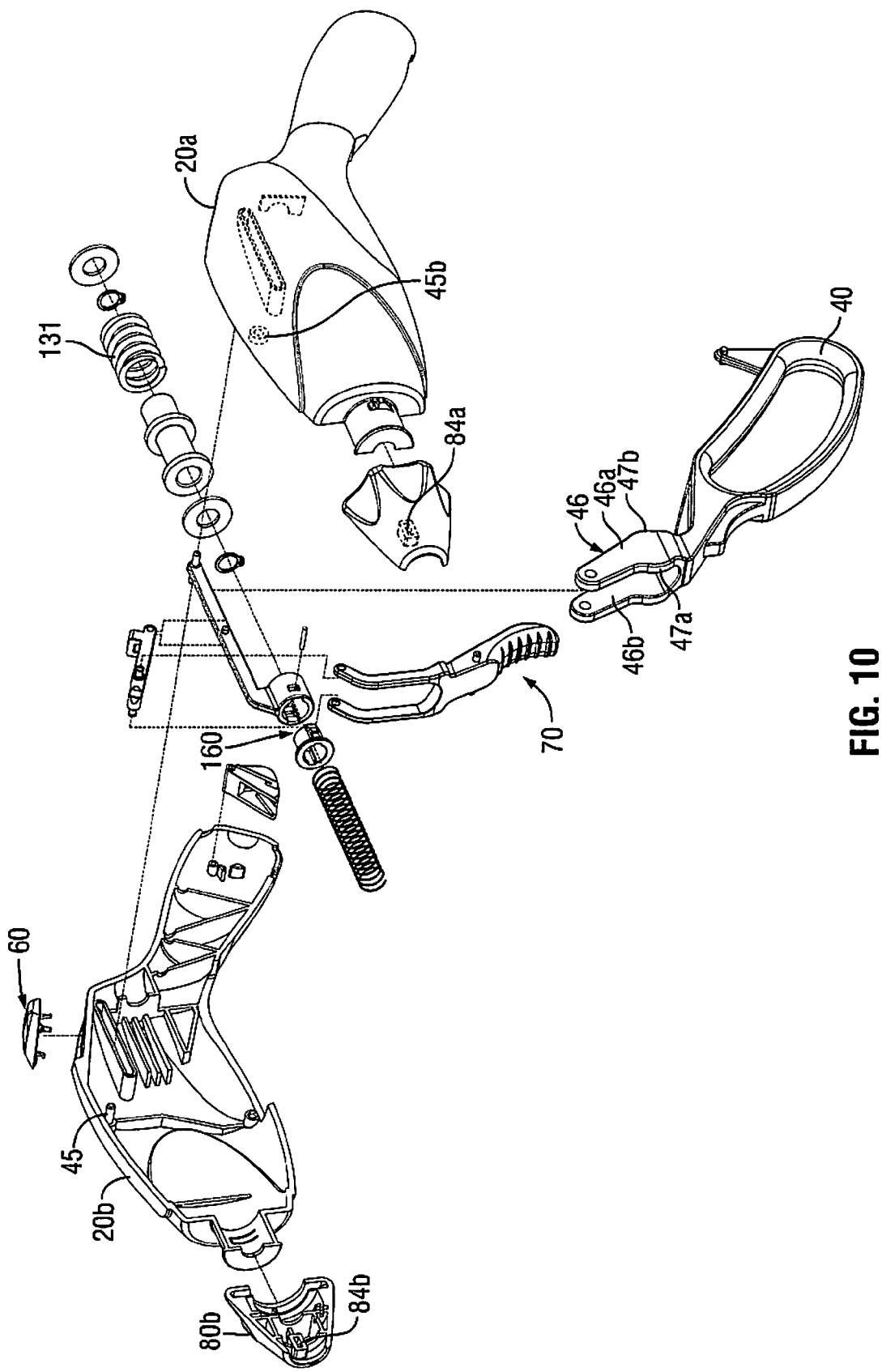
FIG. 10 is an enlarged, exploded perspective view of the housing.

As best seen in FIGS. 9 and 10, rotating assembly 80 includes two C-shaped halves 80a and 80b which, when assembled, form the rotating assembly 80 (See FIG. 1A) which, in turn, house the drive assembly 130 and the knife actuating assembly 160. Half 80a includes a series of detents/flanges (not shown) which are dimensioned to engage a pair of corresponding sockets or other mechanical interfaces (not shown) disposed within rotating half 80b.

Half 80a also includes a tab 84a (phantomly illustrated in FIG. 10) which together with a corresponding tab 84b disposed on half 80b cooperate to matingly engage slot 80' disposed on shaft 12. As can be appreciated, this permits selective rotation of the shaft 12 about axis "A-A" by manipulating the rotating member 80 in the direction of the arrow "B", which, in turn, rotates the end effector assembly in the direction of arrow "C" (See FIG. 1A). The rotating assembly may include one or more mechanical interfaces which essentially lock the rotating assembly in a fully counter-clock wise rotational position or a fully clockwise rotational position. It is envisioned that this will allow left-handed or right-handed orientations for the end effector assembly for particular users.

As best shown in FIGS. 4A, 4B, 5A, 7A, 7B, 9 and 10, trigger assembly 70 mounts atop movable handle 40 and cooperates with the knife assembly 160 to selectively translate knife 190 through a tissue seal. The trigger assembly 70 is initially prevented from firing by the locking flange 49' disposed on movable handle 40 which abuts against the trigger assembly 70 prior to actuation. Details relating to the operation of the trigger assembly are disclosed in U.S. patent application Ser. No. 11/595,194.

Once the desired position for the sealing site is determined and the jaw members 110 and 120 are properly positioned, handle 40 may be compressed fully such that handle 40 locks relative to handle 50 which, in turn, locks the jaw members 110 and 120 in a closed position against the tissue. At this point the jaws members 110 and 120 are fully compressed about the tissue. Moreover, the forceps 10 is now ready for selective application of electrosurgical energy and subsequent separation of the tissue.

As can be appreciated, the combination of the mechanical advantage of the over-the-center pivot along with the compressive force associated with the compression spring 131 facilitate and assure consistent, uniform and accurate closure pressure about the tissue within the desired working pressure range of about 3 kg/cm$^2$ to about 16 kg/cm$^2$ and, desirably, about 7 kg/cm$^2$ to about 13 kg/cm$^2$. By controlling the intensity, frequency and duration of the electrosurgical energy applied to the tissue, the user can treat tissue, i.e., seal tissue.

As mentioned above, at least one jaw member, e.g., 120, may include one or more stop members 90 which limit the movement of the two opposing jaw members 110 and 120 relative to one another. In one within the range from about 0.001 inches to about 0.006 inches and, desirably, between about 0.002 and about 0.005 inches.

As energy is being selectively transferred to the end effector assembly 100, across the jaw members 110 and 120 and through the tissue, a tissue seal forms isolating two tissue halves. When activated via the trigger assembly 70, the knife 190 progressively and selectively divides the tissue along an ideal tissue plane in a precise manner to effectively and reliably divide the tissue into two sealed halves.

Switch 60 is ergonomically dimensioned and conforms to the outer shape of housing 20 (once assembled). Switch 60 is designed to electromechanically cooperate with a flex circuit 400 (See FIG. 7B) to allow a user to selectively activate the jaw members 110 and 120. It is contemplated that a flex circuit design facilitates manufacturing due to the circuits unique ability to conform as needed into tightly spaced areas. It is also envisioned that the switch 60 permits the user to selectively activate the forceps 10 in a variety of different orientations, i.e., multi-oriented activation or toggle-like activation. As can be appreciated, this simplifies activation. It is envisioned that switch 60 may also be designed as a so called "dome switch" which also provides tactile feedback to the user when activated.

When switch 60 is depressed, trigger lead 310b carries the first electrical potential to jaw member 110 thus completing a bipolar circuit. More particularly, when switch 60 is depressed and flex circuit 400 is activated, the generator recognizes a voltage drop across leads 310a and 310c (See FIG. 7B) which initiates activation of the generator 500 to supply a first electrical potential to jaw member 110 and a second electrical potential to jaw member 120. Switch 60 acts as a control circuit and is protected or removed from the actual current loop which supplies electrical energy to the jaw members 110 and 120. This reduces the chances of electrical failure of the switch 60 due to high current loads during activation. A footswitch (not shown) which may also be utilized with the forceps 10, also operates in a similar manner, i.e., upon activation of the footswitch, the generator recognizes a voltage drop across the input and output leads of the footswitch which, in turn, signals the generator to initiate electrosurgical activation of the jaw members 110 and 120. A safety switch or circuit (not shown) may be employed such that the switch cannot fire unless the jaw members 110 and 120 are closed and/or unless the jaw members 110 and 120 have tissue held therebetween.

The forceps 10 may also include a safety circuit that is configured to limit the possibility of disposable forceps 10 being utilized for a second surgery to reduce the risk of a patient being exposed to a non-sterile device. In one embodiment, the safety circuit includes a time-out device 850 (See FIGS. 1A and 1B) that initiates upon initial use and allows the forceps 10 to remain activatable for a pre-set period of time, e.g., 2, 4, 6 12 hours, and then "times out" thereby disabling the forceps 10 from further activation. The time out device 850 may include a mechanical lockout, an optical lockout or an electrical lockout or a combination thereof. With respect to a mechanical lockout, the forceps may include a ruptureable membrane that upon initiation decays over a give time frame. Once the decay reaches a particular threshold (after a predetermined time limit), the device is locked out from further use. The decay may be initiated upon rupture and be reactive to air or a chemical disposed within the forceps 10. A simple mechanical timer may also be utilized or a mechanical decaying pin or element may be utilized that decays over the course of several hours when exposed to ambient air, temperature and/or a particular fluid contained in the mechanical time out device when exposed thereto.

As best described below, the time-out device 850 may include an timing activator 855, e.g., a grenade or timing pin (860), a battery pull-sleeve, electrically insulative cover, or the like, that must be activated before the forceps 10 initial use. Once activated the forceps 10 may be utilized in a normal fashion (as described above) until the pre-set time limit has expired where by the forceps 10 "times out" thereby disabling the forceps 10 from further use.

As can be appreciated, various types of time-out devices 850 may be employed to accomplish this purpose and include, timing circuits, PIC microcontrollers, electromechanical timers, capacitors, batteries, etc. Moreover, the presently-disclosed time-out device 850 may be employed with all types of disposable instruments and not just limited to the instruments described herein, e.g., electrosurgical pencils, ablation devices, coagulators, electrosurgical scissors, return pads, gas-enhanced surgical instrumentation, etc. Moreover, the time-out device 850 may be employed within these electrical instruments (as described above), in the electrical connectors associated with the instruments, or within the generator 500 attached to the instrument. A time-out device 850 may also be employed with the partially disposable instrument or reposable instrument. In this instance, the time-out device 850 may associated with the disposable portion (in this case would be configured in manner similar to above) or be hard-wired into the reposable portion whereby the time-out device 850 is reset each time the disposable portion of the instrument is replaced.

Figure 14:
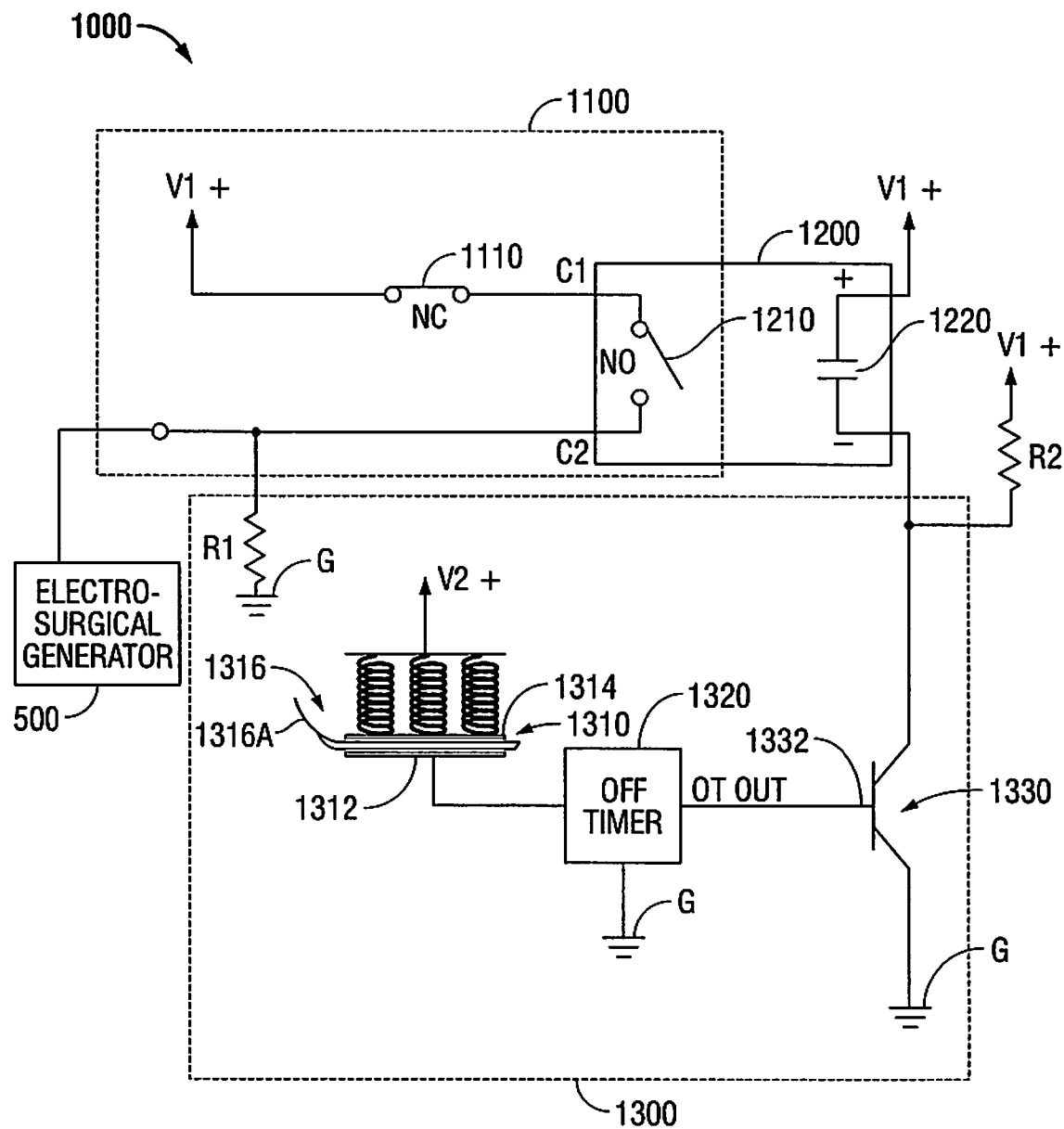
FIG. 14 shows a schematic view of a time-out device including a device activation and use limiting circuit.

An electrical timing or limiting circuit may be configured to prevent activation of the electrosurgical generator after a pre-determined time limit or the timing or limiting circuit may be configured to prevent activation of the activation element after a pre-determined time limit. For example, in one embodiment time-out device 850 (See FIGS. 1A and 1B) includes a device activation and use limiting circuit 1000 as illustrated in FIG. 14. Device activation and use limiting circuit 1000 includes an activation circuit 1100, a control relay 1200 and a timer circuit 1300.

Activation circuit 1100 includes a normally closed (NC) activation switch 1110 electrically connected between a power signal "V1" and a first contact "C1" of a normally open (NO) control relay contact 1210. NC Activation switch 1110 may be switch 60 (See FIG. 7A) or may be a separate switch incorporated into, or actuated by, switch 60. Power signal "V1" may be a control power signal supplied from the electrosurgical generator 500.

The second contact "C2" of the NO control relay contact 1210 connects to the electrosurgical generator 500 and provides a treatment device indicator signal thereto. The treatment device indicator signal, provided to the electrosurgical generator 500, indicates at least one parameter related to the status of the treatment device, e.g., forceps 10 of FIG. 1A. For example, in a "normal" condition the treatment device indicator signal provides an "on" signal, or a signal related to the power signal "V1" (e.g., the power signal is passed through the NC activation switch 1110 and through the NO control relay contact 1210 in a closed position).

A "treatment" condition occurs when the treatment device indicator signal transitions from an "on" signal to an "off" signal (e.g., the NC activation switch 1110 is momentarily opened). This condition may occur when a clinician depresses the NC activation switch 1110 resulting in the electrosurgical generator 500 and forceps 10 performing a treatment cycle. A "fail" condition occurs when the treatment device indicator signal remains low (e.g., the NC activation switch 1110 remains open or the NO control relay contact 1210 remains open). The electrosurgical generator 500 monitors the state or condition of the treatment device indicator signal and may generate an alarm, alert or warning based on the amount of time that the treatment device indicator signal remains low. For example, time that the treatment device indicator signal remains low exceeds a predetermined threshold, the electrosurgical generator 500 may disable the electrosurgical signal output and/or may display an error message indicating that the treatment device 10 has failed.

A "fail" condition may occur if, in the activation switch circuit 1100, the NC activation switch 1110 fails in an open condition or the clinician continues to depress the activation switch 1100 after a treatment cycle is initiated or the NO control relay contact 1210 of the control relay 1200 is open (i.e., the control relay 1200 does not close or energize the circuit). Pull-down resistor "R1" pulls the treatment device indicator signal to ground when the NC activation switch 1110 is open or the NO control relay contact 1210 is open.

The control relay 1200 includes a NO control relay contact 1210 as described hereinabove. The state or condition of the NO control relay contact 1210 is determined by the control relay 1200 control contact 1220. The control contact 1220 closes the NO control relay contact 1210 when a voltage potential is provided between the positive "+" and negative "−" inputs of the control contact 1220. The control contact 1220 can be switched to an "off" condition by removing one of the power signal "V1" from the positive "+" input or the ground connection "G" on the negative "−" input. One suitable control relay 1200 is a LCA110 solid state relay manufactured by Clare Microchips of Beverly, Mass.

Power signal "V1" connects to the positive "+" input of the control contact 1220 and the timer circuit 1300 is configured to provide a ground connection "G" to the negative "−" input of the control contact 1220. If a ground connection "G" is not provided to the control contact 1220 from the timer circuit 1300, the voltage of the negative "−" input of the control contact is pulled up to the power signal voltage "V1" through the control relay 1200 pull-up resistor R2.

Timer circuit 1300 is configured to prevent re-use of the forceps 10 after a pre-determined time limit. In one embodiment, the timer circuit 1300 includes a timer power supply "V2", a pull-tab switch 1310, an off-timer 1320 and a timer control transistor 1330. Timer circuit 1300, once enabled, provides a ground connection "G" to the negative "−" input of the control contact 1220 for a predetermined period of time. Providing a ground connection "G" to the negative "−" input provides a voltage potential across the control contact 1220 which closes the NO control relay contact 1210 thereby allowing the treatment device indicator signal to go high as discussed hereinabove. After a predetermined period of time (i.e., the off-timer expires) the ground connection "G" is disconnected by the timer circuit 1300 and the NO control relay contact 1210 provides an open in the activation circuit 1100 and the treatment device indicator signal goes low as discussed above.

The pull-tab switch 1310 is positioned between the timer power supply "V2" and the off-timer 1320. The pull-tab switch 1310 includes a fixed lower plate 1312, a tensioned upper plate 1314 and a pull-tab 1316 positioned therebetween. Pull-tab 1316 is formed of one or more layers of an electrical insulating material and capable of electrically isolating the fixed lower plate 1312 from the tensioned upper plate 1314. Tensioned upper plate 1314 compresses the pull-tab 1316 against the fixed lower plate 1312.

Timer power supply "V2" may include a battery or power may be supplied from the electrosurgical generator 500 or from any other suitable source of electrical power. In one embodiment, the timer power supply "V2" is a 3V lithium battery capable of supplying a sustainable amount of stored energy to power the timing circuit 1300 for a predetermined period of time. Pull-tab 1316 isolates the battery, thereby conserving the battery, until the pull-tab is removed and the forceps 10 is made operable.

Pull-tab switch 1310 may include any suitable switch capable of connecting the timer power supply "V2" to the timing device provided that the switch, when activated, cannot be deactivated.

The output of the off-timer "OT Out" connects to the gate 1332 of the timer control transistor 1330. When the output of the off-timer "OT Out" is low (i.e., in an off condition) the gate 1332 of the timer control transistor 1330 is closed and the timer control transistor 1330 does not provide a ground connection "G" to negative "−" input of the control relay 1200 control contact 1220. When the output of the off-timer "OT Out" is high (i.e., an on condition) the gate 1332 of the timer control transistor 1330 is open and the timer control transistor 1330 provides a ground connection "G" to the negative "−" input of the control relay 1200 control contact 1220.

The pull-tab 1316 electrically insulates the tensioned upper plate 1314 from the fixed lower plate 1312 and isolates the timer power supply "V2" from the off-timer 1320. The pull-tab 1316 is placed between the tensioned upper plate 1314 and the fixed lower plate 1312 during assembly and/or manufacturing. Without power being provided to the off-timer 1320, the output of the off-timer "OT Out" is low and the treatment device indicator signal is off. The timer control transistor 1330 is open and the pull-up resistor R2 pulls the negative "−" input of the control contact 1200 to the voltage of the power signal V1 thus leaving open the NO control relay contact 1210 of the control relay 1200. As such, the treatment device indicator signal remains low for as long as the pull-tab 1316 of the pull-tab switch 1310 remains positioned between the fixed lower plate 1312 and the tensioned upper plate 1314. As such, the treatment device 10 is disabled (e.g., inoperable) until the pull-tab 1316 is removed from the pull-tab switch 1310.

Pull-tab 1316 may includes a grip tab 1316A configured to be grasped by a clinician and slideably removed from the pull-tab switch 1310. Removal of the pull-tab 1316 from the pull-tab switch 1310 allows the tensioned upper plate 1314 to contact the fixed lower plate 1312 forming an electrical connection therebetween. The pull-tab switch 1310 is configured such that once the pull-tab 1316 is removed, it cannot be repositioned between the tensioned upper plate 1314 and the fixed lower plate 1312.

The treatment device, e.g., forceps 10, is made operable by removing the pull-tab 1316 from between the tensioned upper plate 1314 and fixed lower plate 1312 thereby providing an electrical contact therebetween. Removing the pull-tab 1316 from the pull-tab switch 1310 connects the timer power supply "V2" to the off-timer 1320. When initially powered, the output of the off-timer "OT out" is set high and an internal timer of the off-timer 1320 commences timing. The internal timer of the off-timer 1320 continues timing until the accumulated time of the off-timer accumulator exceeds a threshold. When the off-timer accumulator exceeds a threshold, the output of the off-timer "OT out" is set low, the treatment device indicator signal transitions to a low signal and an error signal may be generate in the electrosurgical generator 500.

In use, the treatment device, e.g., forceps 10, with pull-tab 1316 properly positioned in the pull-tab switch 1310 is inoperable. For example, if a treatment device 10 with a pull-tap 1316 properly positioned in the pull tab switch 1310 is connected to an electrosurgical generator 500 the treatment device indicator signal will remain low and the electrosurgical generator 500 will recognize the forceps 10 as being faulty or defective. The forceps 10 can be made operable by grasping the grip tab 1316A of the pull-tab 1316 and removing the pull-tab 1316 from the pull-tab switch 1310. The forceps 10 remains operable until the accumulated time of the off-timer exceeds a threshold and the timer circuit 1300 disables the forceps 10 from further use. When the accumulated time of the off-timer 1320 exceeds a threshold the treatment device indicator signal transitions from high to low and the forceps 10 become inoperable.

In another embodiment, pull tab switch 1310 may include a power-activated pull tab that is automatically removed from the pull tab switch 1310 when the forceps 10 connects to the electrosurgical generator 500. For example, power-activated pull tab may be configured to evaporate, decompose, disintegrate, dissolve, fragment, or otherwise crumble and/or fall apart when the sealing forceps 10 is connected to the electrosurgical generator 500. In yet another embodiment, timer circuit 1300 may include a time-delayed fuse that is configured to perform the functions of the off-timer 1320.

Figure 15:
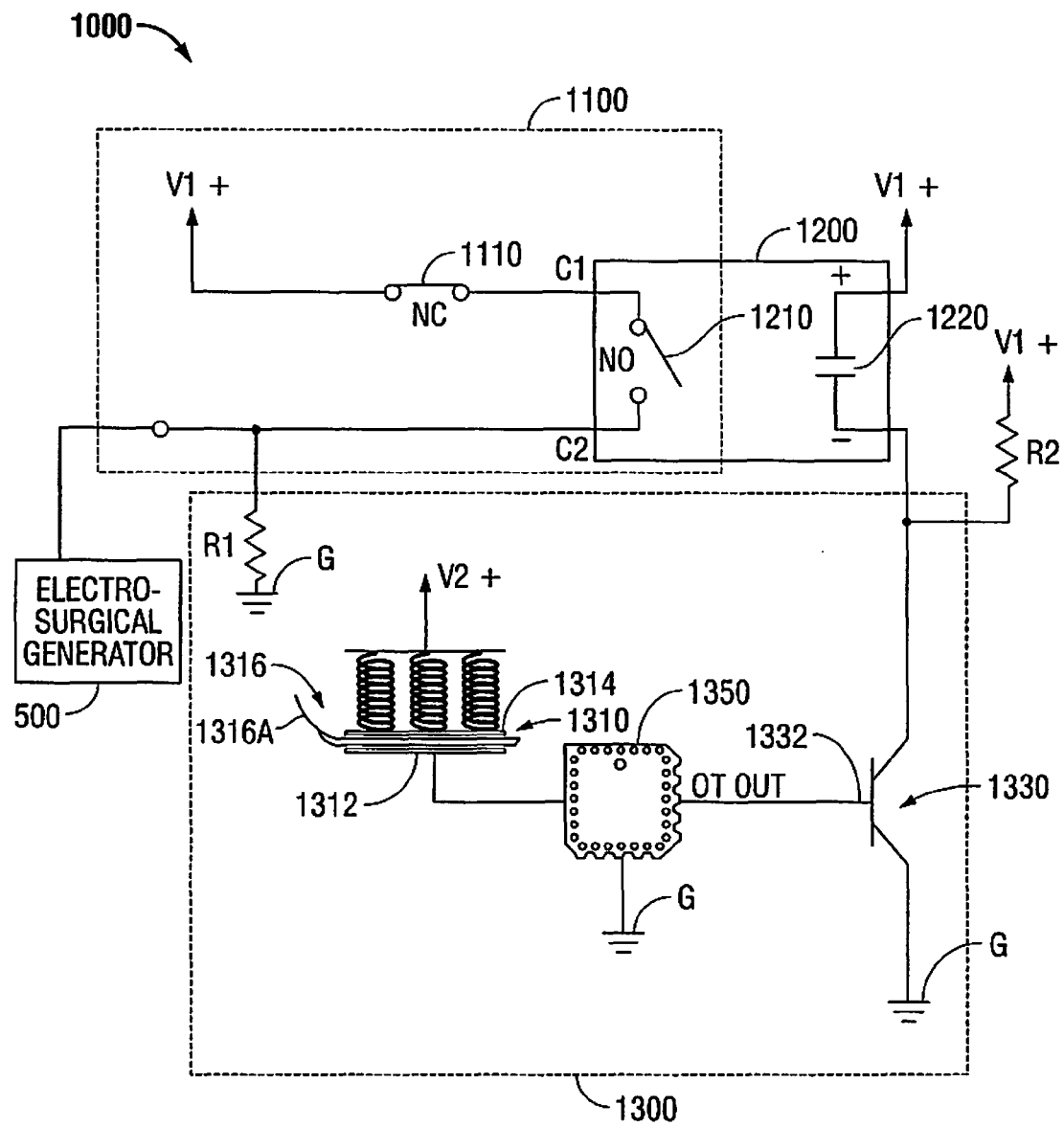
FIG. 15 shows the device activation and use limiting circuit of FIG. 14 including a microcontroller.

In still another embodiment, the timer circuit 1300 may include a time-limiting fuse, a timer limiter, a counter, a microprocessor (with software) or other suitable circuit capable of controlling (i.e., limiting) the amount of time the forceps 10 is used. In one embodiment, the timer circuit 1300 includes a microcontroller 1350, as illustrated in FIG. 15. Microcontroller 1350 may include a 16F690 PIC microprocessor manufactured by Microchip Technology Inc. of Chandler, Ariz. Microcontroller 1350 is configured to execute a software program to perform at least the functions performed by the timer circuit 1300 described hereinabove. In addition to the functionality of the timer circuit 1300 described herein, microcontroller 1350 may also perform additional functions, such as, for example, performing logical operations, collecting and/or storing data, logging information or communicating directly with the electrosurgical generator 500 or other device.

One envisioned embodiment includes a smart recognition connector 900 that validates the forceps 10 for use prior to allowing the forceps 10 to be activated. The smart recognition connector 900 may include an automatic control mechanism 950, e.g., timing circuit, lockout, shut-off, short circuit, etc., that automatically prevents the device from being re-used or an alert mechanism that alerts the surgeon that the device has already been utilized for surgery or is not sterile. Although the below is described with respect to the smart recognition connector, as mentioned above, the forceps 10 may also include any of the envisioned concepts described herein. For example, the timing circuit 1000 may be utilized as explained in detail herein or an expiration sensor, indicator 960, e.g., a color code sensor, may be utilized that changes color if exposed to a non-sterile environment which indicates that the product is no longer sterile due to use, extended shelf life or damage to the sterilization package. The color could be recognized by the surgeon so that the surgeon knows the device is compromised or not sterile or the color could be recognizable by the generator 500 on initial use, e.g., if the device is not sterile a color would appear which is recognized by the generator 500 which prevents activation, e.g., optical lockout.

A color code or an invisible ink printed indicia 965 "DO NOT USE" could appear after a particular amount of time after the device is taken out of the package and exposed to the air (2, 4, 6, 8 hours). The generator 500 or the surgeon recognizes the color or ink indicia and prevents and the instrument is not activated. On this same notion, an invisible bar code 970 could appear after being exposed to air for a given time frame which would prevent the generator from activating the instrument for reuse (the instrument would be usable for an entire procedure but incapable of being reused).

As can be appreciated, the device does not need to be an electrical or electrosurgical device in the case of a color coded or bar coded instrument with manual verification by the surgeon. The surgical team can be trained to recognize a defective, compromised or already used instrument by virtue of a color code or an invisible ink indicia alert.

The present disclosure also relates to a method of performing an electrosurgical procedure including the steps of providing a electrosurgical device in an inoperable condition, making the device operable by enabling a time-out device as described herein, performing at least one electrosurgical procedure and disabling the electrosurgical device as described herein after a predetermined period of time.

The method may include the step of providing an electrosurgical instrument that includes a housing having a treatment portion attached thereto that is adapted to connect to an electrosurgical generator that supplies energy thereto. An activation element is disposed in electrical communication with the electrosurgical generator and the treatment portion. The method may include the step of selectively actuating the electrosurgical generator to supply energy from the electrosurgical generator to the treatment portion. The method may include the step of preventing re-use of the electrosurgical instrument after a pre-determined time limit utilizing a time-out device.

In another embodiment, the method includes the step of providing an electrosurgical instrument that includes a housing having a treatment portion attached thereto and an activation element that is disposed in electrical communication with the electrosurgical generator and the treatment portion. A smart connector is connected to the housing and is adapted to connect to the electrosurgical generator selectively activating the electrosurgical generator to supply energy from the electrosurgical generator to the treatment portion. The method may include the step of preventing re-use of the electrosurgical instrument after a pre-determined time limit by utilizing a time-out device coupled to the smart connector. The method may include enabling a mechanical lockout that decays when exposed to ambient air, temperature and/or fluid, an optical lockout that prevents activation of the electrosurgical generator when activated and/or an electrical lockout that shorts the instrument to prevent re-use.

The method may include the step of providing an electrosurgical instrument, includes a housing having a treatment portion attached thereto, the treatment portion adapted to connect to an electrosurgical generator that supplies energy thereto and a device activation and use limiting circuit. The device activation and use limiting circuit includes an activation circuit, a timer circuit and a control relay connected therebetween. The method may include the step of relaying at least one parameter between the activation circuit and the electrosurgical generator. The method may include the step of providing a timer circuit configured to prevent re-use of the electrosurgical instrument after a pre-determined time limit. The method may include the step of providing a control relay configured to disable the activation circuit after the pre-determined time limit is exceeded. The method may include the step of providing an activation switch configured to indicate activation of the treatment portion.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An electrosurgical instrument comprising:
   a connector configured to releasably connect to an electrosurgical generator;
   a housing adapted to be connected to an electrosurgical generator by the connector and having a treatment portion attached thereto, the treatment portion adapted to connect, through the connector, to an electrosurgical generator that supplies energy thereto;
   an activation element disposed in one of the connector or the housing, the activation element adapted for electrical communication with an electrosurgical generator through the connector and in electrical communication with the treatment portion, the activation element being selectively actuatable to supply energy from an electrosurgical generator to the treatment portion; and
   a time-out device disposed within the housing, the time-out device controlling a flow of electrosurgical energy supplied from an electrosurgical generator through the time-out device and preventing re-use of the electrosurgical instrument after expiration of a pre-determined time limit by disabling activation of the activation element while the activation element receives energy from an electrosurgical generator.

2. The electrosurgical instrument according to claim 1, wherein the time-out device includes a timing circuit adapted for electrical communication with an electrosurgical generator, the timing circuit being initiateable upon initial activation of the electrosurgical instrument and being configured to disable the electrosurgical instrument from future use after a pre-determined time limit.

3. The electrosurgical instrument according to claim 2, wherein the timing circuit further includes:
   a timing activator that includes of at least one of a timing pin, electrically insulative cover and a battery sleeve,
   wherein the timing circuit is initiated upon removal of the timing activator from the electrosurgical instrument.

4. The electrosurgical instrument according to claim 2, wherein the timing circuit prevents activation of an electrosurgical generator after expiration of the pre-determined time limit.

5. The electrosurgical instrument according to claim 2, wherein the timing circuit prevents activation of the activation element after expiration of the pre-determined time limit.

6. The electrosurgical instrument according to claim 1, wherein the time-out device includes at least one of a mechanical lockout, an optical lockout or an electrical lockout.

7. The electrosurgical instrument according to claim 1, wherein the time-out device includes a mechanical lockout that decays when exposed to at least one of ambient air, temperature and fluid.

8. The electrosurgical instrument according to claim 1, wherein the time-out device includes an indicator that appears after expiration of the predetermined time limit thereby indicating that the electrosurgical instrument is inoperable.

9. The electrosurgical instrument according to claim 8, wherein the indicator includes at least one of a color-code, an indicia or a bar code.

10. An electrosurgical instrument, comprising:
   a connector adapted to releasably connect to an electrosurgical generator;
   a housing adapted to be coupled to an electrosurgical generator by the connector and having a treatment portion attached thereto, the treatment portion adapted to connect, through the connector, to an electrosurgical generator that supplies energy thereto;
   an activation element adapted for electrical communication with an electrosurgical generator through the connector and in electrical communication with the treatment portion, the activation element being selectively actuatable to supply energy from an electrosurgical generator to the treatment portion; and
   a time-out device disposed within one of the connector or the housing, the time-out device controlling a flow of electrosurgical energy supplied from an electrosurgical generator through the time-out device and preventing re-use of the electrosurgical instrument after expiration of a pre-determined time limit by disabling activation of the activation element while the activation element receives energy from an electrosurgical generator.

11. The electrosurgical instrument according to claim 10, wherein the time-out device includes at least one of a mechanical lockout, an optical lockout or an electrical lockout.

12. The electrosurgical instrument according to claim 10, wherein the time-out device includes a mechanical lockout that decays when exposed to at least one of ambient air, temperature and fluid.

13. The electrosurgical instrument according to claim 10, wherein the time-out device includes an indicator that appears after the pre-determined time limit has expired thereby indicating that the electrosurgical instrument is inoperable.

14. The electrosurgical instrument according to claim 13, wherein the indicator includes at least one of a color-code, an indicia or a bar code.

15. The electrosurgical instrument according to claim 14, wherein the indicator is adapted to be read by an electrosurgical generator.

16. An electrosurgical instrument, comprising:
   a connector configured to releasably connect to an electrosurgical generator;
   a housing adapted to be coupled to an electrosurgical generator by the connector and having a treatment portion attached thereto, the treatment portion adapted to connect, through the connector, to an electrosurgical generator that supplies energy thereto;
   a device activation and use limiting circuit disposed in one of the connector or the housing including:
      a control relay controlling a flow of electrosurgical energy supplied from an electrosurgical generator through the control relay, the control relay including a timer circuit configured to deactivate the control relay after expiration of a pre-determined time limit and to prevent the flow of electrosurgical energy supplied from an electrosurgical generator through the control relay to the treatment portion while the control relay receives electrosurgical energy supplied from the electrosurgical generator; and
      an activation circuit coupled to the control relay, the activation circuit configured to receive electrosurgical energy transferred from the control relay.

17. The electrosurgical instrument according to claim 16, wherein the activation circuit further includes:
   an activation switch configured to indicate activation of the treatment portion.

18. The electrosurgical instrument according to claim 16, wherein the timer circuit further includes:
   a timer power supply;
   a timing device configured to determine whether the pre-determined time limit has been exceeded; and
   a timer enable switch configured to connect the timer power supply to the timing device,
   wherein the electrosurgical instrument is made inoperable if the pre-determined time limit has been exceeded.

19. The electrosurgical instrument according to claim 18, wherein the timer enable switch, when activated, cannot be deactivated.

20. The electrosurgical instrument according to claim 19, wherein the timer enable switch further includes:
   a removal pull tab configured to enable the timer enable switch when removed therefrom.

21. The electrosurgical instrument according to claim 19, wherein the timing device includes an off-timer.

22. The electrosurgical instrument according to claim 19, wherein the timing device includes a microcontroller.

23. The electrosurgical instrument according to claim 18, wherein the timer power supply is a battery.

* * * * *